(12) United States Patent
Spriewald et al.

(10) Patent No.: US 11,365,172 B2
(45) Date of Patent: Jun. 21, 2022

(54) PRODUCTION PLANT FOR PRODUCING A CHEMICAL PRODUCT BY REACTING H-FUNCTIONAL REACTANTS WITH PHOSGENE, AND METHOD FOR OPERATING SAME WITH AN INTERRUPTION TO PRODUCTION

(71) Applicant: Covestro Deutschland AG, Leverkusen (DE)

(72) Inventors: Juergen Spriewald, Seabrook, TX (US); Thomas Knauf, Dormagen (DE); Dirk Manzel, Moers (DE); Peter Plathen, Krefeld (DE)

(73) Assignee: Covestro Deutschland AG, Leverkusen (DE)

( * ) Notice: Subject to any disclaimer, the term of this patent is extended or adjusted under 35 U.S.C. 154(b) by 329 days.

(21) Appl. No.: 16/622,585

(22) PCT Filed: Jun. 29, 2018

(86) PCT No.: PCT/EP2018/067569
§ 371 (c)(1),
(2) Date: Dec. 13, 2019

(87) PCT Pub. No.: WO2019/007834
PCT Pub. Date: Jan. 10, 2019

(65) Prior Publication Data
US 2021/0147346 A1 May 20, 2021

(30) Foreign Application Priority Data
Jul. 3, 2017 (EP) .................... 17179378

(51) Int. Cl.
| C07C 263/10 | (2006.01) |
| B01D 3/14 | (2006.01) |
| B01D 53/14 | (2006.01) |
| B01J 19/00 | (2006.01) |
| C07C 263/20 | (2006.01) |

(52) U.S. Cl.
CPC ......... *C07C 263/10* (2013.01); *B01D 3/146* (2013.01); *B01D 53/1406* (2013.01); *B01D 53/1456* (2013.01); *B01D 53/1487* (2013.01); *B01D 53/1493* (2013.01); *B01J 19/002* (2013.01); *C07C 263/20* (2013.01); *B01D 2252/103* (2013.01); *B01J 2219/002* (2013.01); *B01J 2219/00225* (2013.01)

(58) Field of Classification Search
CPC ........... C07C 263/10; C07C 265/14; C07C 263/20; B01D 2252/103; B01D 3/146; B01D 53/1406; B01D 53/1456; B01D 53/1487; B01D 53/1493; B01J 19/002; B01J 2219/002; B01J 2219/00225; C08G 64/205
See application file for complete search history.

(56) References Cited

U.S. PATENT DOCUMENTS

| 4,764,308 | A | 8/1988 | Sauer et al. |
| 4,851,570 | A | 7/1989 | Zaby et al. |
| 5,599,968 | A | 2/1997 | Bankwitz et al. |
| 7,118,653 | B2 | 10/2006 | Brady et al. |
| 7,442,835 | B2 | 10/2008 | Keggenhoff et al. |
| 7,524,405 | B2 | 4/2009 | Sohn et al. |
| 7,584,629 | B2 | 9/2009 | Sohn et al. |
| 7,649,108 | B2 | 1/2010 | Schal et al. |
| 2004/0167354 | A1 | 8/2004 | Biskup et al. |
| 2006/0025556 | A1 | 2/2006 | Koch et al. |
| 2006/0123842 | A1 | 6/2006 | Sohn et al. |
| 2007/0261437 | A1 | 11/2007 | Boonstra et al. |
| 2007/0299279 | A1 | 12/2007 | Pohl et al. |
| 2009/0175121 | A1 | 7/2009 | Rausch et al. |
| 2009/0209784 | A1 | 8/2009 | Lorenz et al. |
| 2010/0152484 | A1 | 6/2010 | Biskup et al. |
| 2010/0298596 | A1 | 11/2010 | Keggenhoff et al. |
| 2012/0095225 | A1* | 4/2012 | Yamaura ............ C07D 251/34 544/221 |
| 2017/0101367 | A1 | 4/2017 | Knauf et al. |
| 2017/0152210 | A1* | 6/2017 | Knauf .................. C07C 205/06 |
| 2018/0290968 | A1 | 10/2018 | Knauf et al. |

FOREIGN PATENT DOCUMENTS

DE    2344217    *   3/1975

OTHER PUBLICATIONS

DE2344217 translated (Year: 1975).*
International Search Report; International Application No. PCT/EP2018/067569; dated Sep. 17, 2018; Authorized Officer: Schlicke, Benedikt.

* cited by examiner

*Primary Examiner* — Jafar F Parsa
*Assistant Examiner* — Blaine G Doletski
(74) *Attorney, Agent, or Firm* — Donald R. Palladino

(57) ABSTRACT

The invention relates to a method for operating a production plant for producing a chemical product (1) by reacting a H-functional reactant (2) with phosgene (3) during an interruption in production when taking at least one plant part of the production plant out of operation, wherein low-oxygen and oxygen-rich phosgene-containing exhaust gas flows are directed separately from one another in different phosgene decomposition directions and separately from one another—at spatially different points—into a combustion device, wherein plant parts that have not been taken out of operation are operated in a closed-circuit operating mode. The invention also relates to a production plant for producing a chemical product by reacting H-functional reactants with phosgene, which is suitable for being operated with the method according to the invention.

17 Claims, 6 Drawing Sheets

PRODUCTION PLANT FOR PRODUCING A CHEMICAL PRODUCT BY REACTING H-FUNCTIONAL REACTANTS WITH PHOSGENE, AND METHOD FOR OPERATING SAME WITH AN INTERRUPTION TO PRODUCTION

CROSS-REFERENCE TO RELATED APPLICATION

This application is a national stage application under 35 U.S.C. § 371 of PCT/EP2018/067569, filed Jun. 29, 2018, which claims the benefit of European Application No. 17179378.9, filed Jul. 3, 2017, both of which are incorporated by reference herein.

FIELD

The invention relates to a method of operating a production plant for preparation of a chemical product (1) by reacting an H-functional reactant (2) with phosgene (3) in the event of a production stoppage with shutdown of at least one plant component of the production plant, in which low-oxygen and oxygen-rich phosgene-containing offgas streams are guided separately into different phosgene breakdown directions and separately—at spatially different points—into an incineration unit, wherein plant components that have not been shut down are operated in circulation mode. The invention further relates to a production plant for preparation of a chemical product by reacting H-functional reactants with phosgene, which is suitable for operation by the method of the invention.

BACKGROUND

In many industrial production processes, especially production processes for chemical products, gaseous process products other than the actual product of the production process are obtained, which, before they are released as offgases into the environment, have to be processed in order to minimize economic losses and damage to the environment. Such workup steps may include various processes. Examples of such cleaning operations include scrubbing, absorption (for example of $NO_x$), adsorption, condensation and filtration. It is customary in the prior art to combine such gaseous process products that have been subjected to preliminary cleaning in this way on conclusion of all cleaning operations conducted for preliminary cleaning (and possibly even beforehand) and to send the offgas stream thus obtained to a common offgas incineration in which the offgas is combusted sufficiently completely that the incineration gases (if required after further cleaning, for example a base scrubbing to bind acidic constituents) can be released into the environment while complying with official environmental regulations.

One example of an industrial production process in which gaseous process products are obtained is the production of isocyanates by phosgenation of the corresponding amines. In the phosgenation, a gaseous process stream comprising the hydrogen chloride co-product and unconverted phosgene is obtained. Residues of the solvent used (and also inerts or else excess carbon monoxide from the phosgene preparation) are regularly also present therein. Workup steps that follow may give further gaseous process products, some of which also contain solvent. In this connection, the recovery of solvent from the various gaseous process products obtained at different points in the process is important. Processes for solvent recovery via distillation in isocyanate production processes are addressed, for example, by EP 1 575 908 B2 and EP 1 575 906 B1.

In addition to the recovery of solvent, maximum recovery of the hydrogen chloride coproduct and of the excess phosgene plays an important role. WO 2004/056758 A1 describes further purification of hydrogen chloride from hydrogen chloride/phosgene separation by adsorption of impurities (residues of phosgene and chlorobenzene) on activated carbon.

Once all products of value have been recovered as far as possible from the gaseous process streams obtained, what remains is an offgas stream that may still contain trace fractions of phosgene and therefore passes through a phosgene breakdown before introduction into the offgas incineration. It is customary in the prior art to combine the offgas streams obtained and send the overall offgas stream thus obtained to a common phosgene breakdown and then to incineration. In regular operation, this procedure is generally entirely satisfactory. However, problems occur when production has to be stopped temporarily, for example to conduct repair operations on a plant component. If the repair measure does not take too long, it is appropriate in such a case not to shut down the entire production plant, but only the plant component affected by the repair measure, while the remaining plant components are operated further in what is called circulation mode without preparation of the desired target product. This procedure is outlined in WO 2015/197522 A1 for the production of chemical products in general, and in WO 2017/050776 A1 for the production of isocyanates in particular. Offgas streams may also still be obtained in the plant components operated in circulation mode, if only because the conduits that connect these plant components to the offgas system preferably also remain open during the circulation mode in order to enable "breathing" of the plant. The offgas streams obtained here are low in oxygen or even oxygen-free. In the plant component that has been shut down for repair purposes, however, oxygen-rich offgas streams may be obtained (for example as a result of suction operated for reasons of occupational safety), which, for safety reasons, likewise pass through the phosgene breakdown and are incinerated. But these oxygen-rich offgas streams cannot be combined directly with the aforementioned low-oxygen offgas streams, but rather only after sufficient dilution, for example with nitrogen, to prevent the formation of an explosive gas mixture. But this dilution incurs additional costs resulting from the provision of the diluent gas itself, the need to handle larger volume flows, problems in the incineration owing to an increased inert gas fraction compared to regular operation, and so forth. These problems can only be avoided according to prior art in the event of shutdown of the entire production plant because exclusively oxygen-rich offgas streams are obtained in this case. But this dispenses with the possibility of utilizing the economic advantages of the abovementioned circulation mode. This dilemma, described using the example of isocyanate preparation, occurs in the preparation of all chemical products that are obtained by phosgenation of compounds with H-functional reactants.

SUMMARY

It would therefore be desirable to have available a method of operating production plants for preparation of chemical products by reacting H-functional reactants with phosgene in the event of a production stoppage that offers a way out of this problematic situation.

Taking account of this need, the present invention provides a method of operating a production plant for preparation of a chemical product (1) by reacting an H-functional reactant (2) with phosgene (3) in the event of a production stoppage, wherein the production plant has the following plant components:

A) a reaction section (1000) suitable for reacting an H-functional reactant (2) with phosgene (3), having:
  A.I) a mixing zone (1100) for mixing the H-functional reactant (2) and phosgene (3) to give a reaction mixture (50),
  A.II) a reaction zone (1200) connected to the mixing zone (1100) for reacting the reaction mixture (50) obtained in A.I) to form a liquid phase (60) comprising the chemical product (1) and phosgene (3) and a phosgene-containing process offgas stream (70);
B) a workup section (2000) connected to the reaction section (1000) and having:
  B.I) a separation unit (2100-2500) for separating the liquid phase (60) obtained in A.II) into a phosgene-containing process offgas stream (170) and into a liquid phase (100) comprising the chemical product (1);
C) an offgas workup section (3000) suitable for workup of phosgene-containing offgas streams obtained during the preparation of the chemical product (1) and during the production stoppage, comprising a first phosgene breakdown unit (3011) and a second phosgene breakdown unit (3012), where the first and second phosgene breakdown unit are configured to receive inflow of phosgene-containing offgas streams independently of one another;
D) an incineration unit (6000) suitable for incineration of the worked-up offgas obtained in the offgas workup section (3000);
  wherein phosgene (3) is used in a stoichiometric excess relative to all active hydrogen atoms of the H-functional reactants during the preparation of the chemical product (1) in the reaction section (1000), wherein the phosgene-containing process offgas stream (70) obtained from A.II) in the reaction zone (1200) and the phosgene-containing process offgas stream (170) obtained from B.I) in the separation unit (2100-2500), each optionally after passing through further workup steps, are sent to the first phosgene breakdown unit (3011),
  wherein the production of the chemical product (1) is also interrupted temporarily by switching off the supply of the H-functional reactant (2), wherein, during this production stoppage,
    at least one plant component of A) and/or B) is shut down and, in at least one of the plant components that have not been shut down, an output stream from this at least one plant component that has not been shut down is conducted
    (i) into the respective plant component or
    (ii) into an upstream or downstream plant component and thence, optionally via further plant components that have not been shut down, recycled into the original plant component
    and hence the respective plant component is put in circulation mode, wherein process offgas is obtained in the at least one plant component put in circulation mode and oxygen-containing offgas (400-X) is obtained in the at least one plant component that has been shut down;
  process offgas from the at least one plant component that has been put in circulation mode is conducted into the first phosgene breakdown unit (3011), wherein the first phosgene breakdown unit (3011) remains in operation even during the production stoppage;
  oxygen-containing offgas (400-X) from the at least one plant component that has been shut down is supplied to the second phosgene breakdown unit (3012), wherein the second phosgene breakdown unit (3012) is in operation at least during the production stoppage, wherein
  process offgas (210-X) that has been freed of phosgene from the first phosgene breakdown unit (3011) and oxygen-containing offgas (410-X) that has been freed of phosgene from the second phosgene breakdown unit (3012) are supplied separately to and combusted in the incineration unit (6000) at spatially separate points.

The invention further relates to a production plant for preparation of a chemical product (1) by reacting an H-functional reactant (2) with phosgene (3), having the following plant components:

A) a reaction section (1000) suitable for reacting an H-functional reactant (2) with phosgene (3), having:
  A.I) a mixing zone (1100) for mixing the H-functional reactant (2) and phosgene (3) to give a reaction mixture (50),
  A.II) a reaction zone (1200) connected to the mixing zone (1100) for reacting the reaction mixture (50) obtained in A.I) to form a liquid phase (60) comprising the chemical product (1) and phosgene (3) and a phosgene-containing process offgas stream (70);
B) a workup section (2000) connected to the reaction section (1000) and having:
  B.I) a separation unit (2100-2500) for separating the liquid phase (60) obtained in A.II) into a phosgene-containing process offgas stream (170) and into a liquid phase (100) comprising the chemical product (1);
C) an offgas workup section (3000) suitable for workup of phosgene-containing offgas streams obtained during the preparation of the chemical product (1) and during the production stoppage, comprising a first phosgene breakdown unit (3011) and a second phosgene breakdown unit (3012), where the first and second phosgene breakdown unit are configured to receive inflow of phosgene-containing offgas streams independently of one another;
D) an incineration unit (6000) suitable for incineration of the worked-up offgas obtained in the offgas workup section (3000), wherein the incineration unit (6000) is connected to the offgas workup section (3000) in such a way that the offgas streams obtained in the first phosgene breakdown unit (3011) and in the second phosgene breakdown unit (3012) are sent separately to the incineration unit (6000);
  wherein the production plant is configured such that, in the event of a production stoppage, by shutting down the supply of the H-functional reactant (2) and shutting down at least one plant component, an output stream from this at least one plant component that has not been shut down is conducted
    (i) into the respective plant component or
    (ii) into an upstream or downstream plant component and thence, optionally via further plant components that have not been shut down, recycled into the original plant component
  and hence the respective plant component can be put in circulation mode,
  wherein the production plant is further configured such that
    process offgas obtained in the at least one plant component put in circulation mode can be conducted into the first phosgene breakdown unit (3100) and oxygen-containing offgas (400-X) obtained in the at least one plant component that has been shut down can be conducted into the second phosgene breakdown unit (3200), without mixing of process offgas and oxygen-containing offgas (400-X) with one another.

BRIEF DESCRIPTION OF THE DRAWINGS

Various features and characteristics of the inventions described in this specification may be better understood by reference to the accompanying figures, in which.

DETAILED DESCRIPTION

Figure 1A:
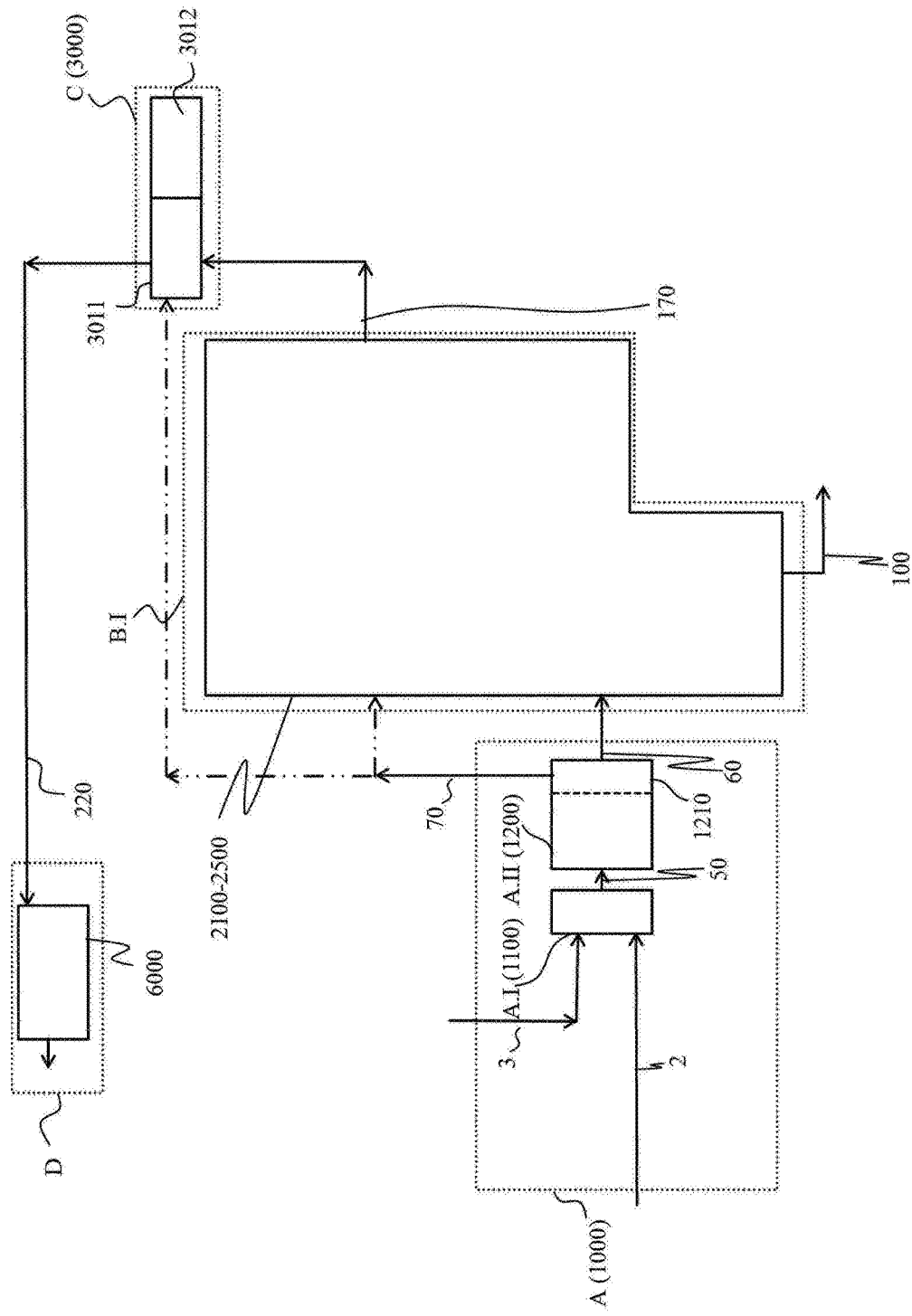
FIG. 1a is a schematic illustration of an embodiment of the method of the invention without separation of hydrogen chloride from the process offgas in regular operation.

"H-functional reactants (2)" in the context of the invention are those organic compounds that have at least one hydrogen atom which is bonded to N, O, or S and is capable of reacting with phosgene to release hydrogen chloride (referred to in the context of the invention as "active hydrogen atom"). "Chemical products (1)" in the context of the invention are the organic condensation products formed. The functionality is understood to mean the number of active hydrogen atoms per molecule of the H-functional reactant. In particular embodiments, H-functional reactants may also be used in the form of their salts; this is also considered in accordance with the invention to be encompassed by the expression "H-functional reactant".

The method of the invention is operated continuously in regular operation. This means that the plant components from A) and B), during production, i.e. while the supply of the H-functional reactant is not interrupted (and of course the supply of phosgene is not interrupted), are charged continuously with the appropriate input streams (for example the mixing zone 1100 with the H-functional reactant and phosgene) and respective products are continuously withdrawn therefrom (for example the reaction mixture 50). The same is of course also true of the offgas workup section (3000) from C) and the incineration unit (6000) from D).

The feature of the invention that "the phosgene-containing process offgas stream (70) obtained from A.II) in the reaction zone (1200) and the phosgene-containing process offgas stream (170) obtained from B.I) in the separation unit (2100-2500), each optionally after passing through further workup steps, are sent to the first phosgene breakdown unit (3011)" also includes those embodiments in which one of the two process offgas streams merges into the other. Examples of this are described further down.

In the context of the present invention, in all embodiments, "a plant component from A) and/or B) is shut down".

Such a shutdown of a plant component means stopping it such that an inspection, repair, maintenance or cleaning measure (collectively "measure" henceforth) can be conducted. For this purpose, the supply of the reactants guided into this plant component in regular operation is stopped, and the connection of the plant component in question to the other plant components of the production plant is closed, optionally with the exception of conduits that are required during the measure, for example for flushing the plant component with a cleaning fluid.

According to the invention, the term "shutdown" accordingly encompasses, in the case of presence of n plant components within the meaning of the present invention (in this regard, see also the paragraph which follows), where n is a natural number, the shutdown of a maximum of n−1 of these plant components. According to the invention, at least one plant component is thus not "shut down" in the aforementioned sense (i.e. at least one plant component is not completely stopped). Preferably, the present invention is concerned with the case of shutdown of 1 to 2 plant components, more preferably of 1 plant component. According to the invention, therefore, in the event of shutdown of a plant component (or two or more plant components, but not all plant components), the formation of further product is always stopped (since the supply of the H-functional reactant is stopped and, therefore, no further product can be produced).

"Circulation mode" is understood in the context of this invention to mean that an output stream from a plant component from A) and/or B) is ultimately used again as input stream for this plant component. As a result of the stoppage of production, these streams in circulation mode have a different composition than in regular operation, which is indicated in the context of the present invention by the suffix "-X" to the respective reference numeral. This circulation mode can be implemented in such a way that the output stream is recycled directly back into the same plant component. It is also possible (and preferable) that the output stream from the original plant component is recycled into the original plant component only after passing through one or more further plant components, in which case the further plant component(s) may be connected up- or downstream of the original plant component. The expression "a plant component from A)" may refer either to the reaction section (1000) as a whole (i.e. include A.I) and A.II)) or to each constituent A.I) and A.II) on its own. The same applies to the workup section (2000) (which, in preferred embodiments, may have further constituents B.II) and B.III)). In particular embodiments, plant components may also be constructed from single apparatuses which may then in turn be plant components within the meaning of the invention. In such a case, the circulation mode need not necessarily extend over the (entire) plant component, but may be limited to individual apparatuses thereof, i.e. plant (sub-)components. One example of this is the "separation unit (2100-2500)" from B.I), which may be formed from different subunits (2100, 2200, 2300 and 2500), each of which may in turn be regarded as a plant component within the meaning of the invention, as elucidated in detail further down. Another example of a plant component consisting of multiple apparatuses, in particular embodiments, is the reaction zone (1000), since mixing zone (1100) and reaction zone (1200) may also be part of one and the same apparatus (one and the same plant component), in which case a strict spatial delimitation between the two is no longer possible under some circumstances. A circulation mode of the invention may thus, for example, encompass the entire reaction section (1000) (especially, but without limitation, when mixing zone (1100) and reaction zone (1200) are realized in one apparatus) or else just parts thereof. It is likewise possible that plant components from A) together with plant components from B) are encompassed by a common circulation mode.

Offgas streams which occur in regular operation of the plant or in the above-elucidated circulation mode are referred to in the context of this invention as "process offgas streams" or "process offgas" for short. Such process offgas streams regularly contain oxygen in a minor proportion by volume at most, which is in any case (much) less than that of the oxygen-containing offgas streams described hereinafter. This minor proportion by volume of oxygen at most may originate from a minor oxygen component dissolved in the reactants used or, in the case of plant components operated under reduced pressure, from the vacuum system. Preferably, the proportion by volume of oxygen based on the total volume in such process offgas streams is not more than 3.9%, more preferably not more than 3.0%, even more preferably not more than 2.6%, very exceptionally preferably not more than 2.0%.

Offgas streams that are obtained only in the event of a measure in a plant component that has been shut down, for example as a result of a suction operation implemented for safety reasons, by contrast, will regularly contain considerable proportions of oxygen and are therefore referred to in the context of the present invention as "oxygen-containing offgas streams" or as "oxygen-containing offgas" for short (or in technical jargon as "waste air"). In this context, an offgas stream is oxygen-containing when its proportion by volume of oxygen, based on the total volume, is at least 4.0%.

The person skilled in the art is aware of suitable methods of determining the oxygen content in offgas streams. In principle, standard oxygen determination methods give the same result within the range of variations that are insignificant for the purposes of the present invention. In the case of doubt, the result measured with an oxygen sensor that works on the basis of the paramagnetic alternating pressure method is crucial for the purposes of the present invention. Suitable measurement apparatuses can be sourced, for example, from Siemens (e.g. "Oximat 6").

According to the invention, process offgas streams and oxygen-containing offgas streams are kept separate from the site at which they are formed until introduction into the incineration unit (6000). This is enabled by the use of at least two phosgene breakdown units (3011, 3012, ... ), of which just one (3011) is intended for process offgas and one (3012) for oxygen-containing offgas (i.e. process offgas and oxygen-containing offgas are never introduced into the same phosgene breakdown unit). Dedicated offgas conduits lead from the first phosgene breakdown unit (3011) into the incineration unit (6000), and likewise from the second phosgene breakdown unit (3012) for oxygen-containing offgas into the incineration unit (6000). These separate offgas conduits from the first phosgene breakdown unit (3011) and from the second phosgene breakdown unit (3012) enable guiding a process offgas and oxygen-rich offgas into the incineration without premixing. The offgas conduits for process offgas and for oxygen-containing offgas open into the incineration unit (6000) "at spatially separate points", such that mixing of constituents from the two streams can only set in when the incineration has already set in. The present invention thus makes it possible to keep process offgas and oxygen-containing offgas separate from one another from the point at which each is formed as far as the incineration, which can avoid any risk of explosion without the additional use of an inert diluent gas, for example nitrogen.

There firstly follows a brief summary of various possible embodiments of the invention:

In a first embodiment of the invention, the chemical product (1) is an organic carbonate, especially a polycarbonate.

In a second embodiment of the invention, the chemical product (1) is an isocyanate, especially tolylene diisocyanate or a mixture of methylene diphenylene diisocyanate and polymethylene polyphenylene polyisocyanate.

In a third embodiment of the invention, which is a particular embodiment of the second embodiment, the separation unit (2100-2500) from B.I) has the following:
 a distillation apparatus (2100) for separating the liquid stream (60) into a liquid stream (80) comprising solvent and isocyanate and a gaseous process offgas stream (90) comprising phosgene and hydrogen chloride;
 a distillation apparatus (2200) for separating the liquid stream (80) comprising solvent and isocyanate into a process offgas stream (110) comprising solvent and a liquid stream (100) comprising isocyanate;
 a distillation apparatus (2300) for separating the process offgas stream (110) comprising solvent into a liquid stream (120) comprising solvent and a gaseous, phosgene-containing process offgas stream (130).

In a fourth embodiment of the invention, which is a particular configuration of the third embodiment, the separation unit (2100-2500) from B.I) also has an absorption apparatus (2500) in which the phosgene-containing process offgas streams (70), (90) and (130) are cleaned by absorption in a solvent (4) to obtain a liquid stream (160) comprising solvent and phosgene and a gaseous process offgas stream (170) comprising hydrogen chloride and solvent, wherein the gaseous phosgene-containing process offgas streams (70) and (90) are preferably first combined and the combined phosgene-containing process offgas stream (70) and (90) and the phosgene-containing process offgas stream (130) are each condensed and then introduced in liquid form into the absorption apparatus (2500).

In a fifth embodiment of the invention, which is a particular configuration of the second, third and fourth embodiments, especially of the fourth embodiment, the workup section (2000) from B), in addition to the separation unit (2100-2500) from B.I), has the following:
B.II) a separation unit (2600) for separation of hydrogen chloride from the phosgene-containing process offgas stream (170),
 in which the phosgene-containing process offgas stream (170) is depleted of hydrogen chloride, wherein, preferably after passage through a vapor condenser (2630), a gaseous phosgene-containing process offgas stream (200) comprising solvent and any gaseous secondary components is obtained, wherein the phosgene-containing process offgas stream (200) is sent to the first phosgene breakdown unit (3011).

In a sixth embodiment of the invention, which is a particular configuration of the fifth embodiment, the separation of the hydrogen chloride in the separation unit (2600) is performed by absorption of hydrogen chloride in water or hydrochloric acid at a concentration in the range from 0.50% by mass to 15.0% by mass, based on the total mass of the hydrochloric acid, to obtain a hydrochloric acid-containing stream (190) in addition to the phosgene-containing process offgas stream (200) comprising solvent and any gaseous secondary components.

In a seventh embodiment of the invention, which is a particular configuration of the second, third, fourth, fifth and sixth embodiments, the workup section (2000) from B), in addition to the separation unit (2100-2500) from B.I) and, if present, in addition to the separation unit (2600) from B.II), has the following:

B.III) a distillation unit (2400) for workup of the liquid phase (100) comprising the isocyanate, wherein the distillation unit (2400) is optionally preceded upstream by a unit for removing polymeric isocyanate fractions (2410).

In an eighth embodiment of the invention, which is a particular configuration of the seventh embodiment, the unit for removing polymeric isocyanate fractions (2410) is present, and the following circulation modes are established during a production stoppage:

a first circulation mode proceeding from the top of the distillation apparatus (2200) via the distillation apparatus (2300) back into the distillation apparatus (2200);

a second circulation mode proceeding from the bottom of the distillation apparatus (2200) via the unit for removing polymeric isocyanate fractions (2410) back into the distillation apparatus (2200);

a third circulation mode proceeding from the distillation apparatus (2100) and back into it, and a fourth circulation mode proceeding from the separation unit (2600) for separating hydrogen chloride and back into it, wherein the reaction section (1000) from A) is shut down.

In a ninth embodiment of the invention, which can be combined with all other embodiments, the production plant has a phosgene preparation section (0) comprising an apparatus (4000) for preparation of phosgene from carbon monoxide (300) and chlorine (310), wherein the preparation of phosgene is shut down when production is stopped, optionally with a time delay after the supply of the H-functional reactant (2) has been switched off.

In a tenth embodiment of the invention, which can be combined with all other embodiments, the plant components of the workup section (2000) from B) are operated at least partially at reduced pressure relative to ambient pressure, wherein the reduced pressure is generated by vacuum generation plants in which process offgas streams that are supplied to the first phosgene breakdown unit (3011) are obtained.

In an eleventh embodiment of the invention, which is a particular configuration of the tenth embodiment, the first phosgene breakdown unit (3011) has at least two separately operated phosgene breakdown plant components (3011-1, 3011-2), wherein, during the preparation of the chemical product (1), one of these two phosgene breakdown plant components (3011-1) is supplied solely with the process offgas streams from the vacuum generation plants, while the other phosgene breakdown plant component (3011-2) is supplied with all other process offgas streams, wherein, during a production stoppage, the vacuum generation plants are shut down and remain connected to the phosgene breakdown plant component (3011-1).

In a twelfth embodiment of the invention, which can be combined with all other embodiments, during the production of the chemical product, oxygen-containing offgas streams (410-X) are obtained, wherein the second phosgene breakdown unit (3012) for oxygen-containing offgas streams is operated during the production of the chemical product (1) as well and it is supplied with the oxygen-containing offgas streams (410-X).

In a thirteenth embodiment of the invention, which is a particular configuration of the twelfth embodiment, the second phosgene breakdown unit (3012) comprises at least two phosgene breakdown plant components (3012-1, 3012-2) connected in parallel, wherein one of the phosgene breakdown plant components (3012-1) is supplied solely with the oxygen-containing offgas streams (410-X) obtained during the production of the chemical product, while the other phosgene breakdown plant component (3012-2) is supplied with the oxygen-rich offgas streams (400-X) obtained in at least one plant component that has been shut down in the event of a production stoppage.

The embodiments briefly outlined above and further possible configurations of the invention are elucidated in detail hereinafter. Various embodiments are combinable with one another as desired unless the opposite is clearly apparent to the person skilled in the art from the context.

The method of the invention is fundamentally suitable for preparation of any chemical products (1) that are formed by a condensation reaction of an H-functional reactant with phosgene with elimination of hydrogen chloride. The whereabouts of the hydrogen chloride formed in the condensation reaction depends on the procedure:

i. If the hydrogen chloride is not neutralized and the reaction takes place in the absence of an aqueous medium, hydrogen chloride goes in considerable proportions into the phosgene-containing process offgas stream (70) (as well as any further proportions that may be dissolved in the liquid phase (60)). In this case, the workup section (2000) from B) also includes a plant component B.II), a separation unit (2600) for separation of hydrogen chloride from the phosgene-containing process offgas stream (70) obtained in A.II) (and from the gas phase (170) obtained in B.I), the hydrogen chloride content of which originates from hydrogen chloride dissolved in the liquid phase (60)) to form a phosgene-containing process offgas stream (200) depleted of hydrogen chloride and a hydrogen chloride-containing (or hydrochloric acid-containing) stream (190), as will be explained in more detail below.

ii. If the reaction (a) takes place in the presence of an aqueous medium or (b) the liquid phase (60) containing the chemical product is washed with an aqueous medium immediately after the reaction has ended, an aqueous liquid phase (61) is obtained, into which the hydrogen chloride is transferred. This is the case especially when the aqueous medium contains a base and hence the hydrogen chloride is converted to a salt. Depending on the completeness with which hydrogen chloride is transferred to the aqueous liquid phase (61), it may be possible to dispense with a workup component B.II).

The simplest embodiment of the method of the invention without separation of hydrogen chloride from the process offgas in regular operation is shown in FIG. 1*a*:

The phosgene-containing process offgas stream (70) obtained in the reaction zone (1200) from A.II) or in a separation zone (1210) integrated into the reaction zone is guided into the first phosgene breakdown unit (3011) either directly or after passing through the workup stage B.I). If the workup stage B.I) is implemented, it is appropriate to combine the phosgene-containing process offgas stream (70) with process offgas streams obtained therein, such that the phosgene-containing process offgas stream (70) ultimately becomes part of the phosgene-containing process offgas stream (170).

Figure 1B:
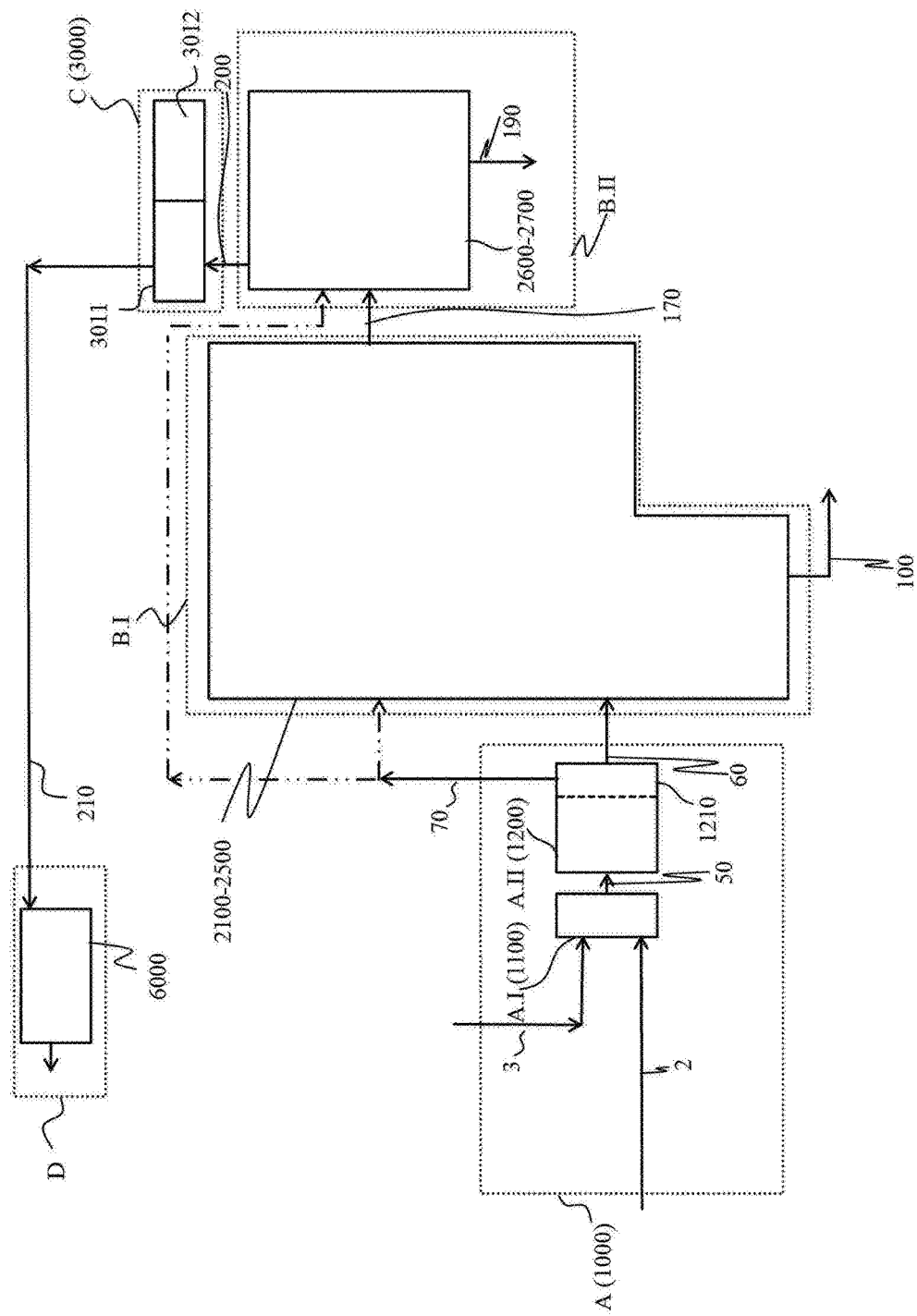
FIG. 1b is a schematic illustration of an embodiment of the method of the invention with separation of hydrogen chloride from the process offgas in regular operation.

FIG. 1*b* shows one embodiment of the method of the invention with separation of hydrogen chloride from the process offgas in regular operation:

The phosgene-containing process offgas stream (70) obtained in the reaction zone (1200) from A.II) or in a separation zone (1210) integrated into the reaction zone is guided into the hydrogen chloride separation unit (2600) from B.II) either directly or after passing through the workup stage B.I). If the workup stage B.I) is implemented, it is appropriate to combine the phosgene-containing process offgas stream (70) with processed offgas streams obtained therein, such that the phosgene-containing process offgas stream (70) ultimately becomes part of the phosgene-containing process offgas stream (170).

Known examples of chemical products (1) obtainable in this way are organic carbonates, especially polycarbonates (by reaction of organic alcohols, especially polyhydric alcohols, with phosgene) and isocyanates (by reaction of organic primary amines with phosgene). Interfacial polycondensation of alcohol salts (2) in basic aqueous solution and phosgene (3) dissolved in an organic solvent (4) for preparation of polycarbonates (1) is an example of the aforementioned method version ii in variant (a). The preparation of isocyanates (1) by phosgenation of the corresponding primary amines (2) is an example of method version i. The invention is elucidated by way of example hereinafter with reference to the preparation of organic carbonates, especially polycarbonates, and isocyanates; however, it is not limited thereto.

The method of the invention is applicable to the preparation methods of any organic carbonates and especially polycarbonates. The method of the invention is preferably used in methods of preparing polycarbonates that derive from bisphenol S, dihydroxydiphenyl sulfide, tetramethylbisphenol A, 1,1-bis(4-hydroxyphenyl)-3,3,5-trimethylcyclohexane (BPTMC), 1,1,1-tris(4-hydroxyphenyl)ethane (THPE) or bisphenol A. Bisphenol A is particularly preferred.

The method of the invention is applicable to the preparation methods of any aromatic, aliphatic and aromatic isocyanates. Preference is given to using the method of the invention for preparation of methylene diphenylene diisocyanate (from methylene diphenylene diamine), polymethylene polyphenylene polyisocyanate (from polymethylene polyphenylene polyamine), mixtures of methylene diphenylene diisocyanate and polymethylene polyphenylene polyisocyanate, tolylene diisocyanate (from tolylenediamine), xylylene diisocyanate (from xylylenediamine), pentane 1,5-diisocyanate (from pentane-1,5-diamine), hexamethylene diisocyanate (from hexamethylenediamine), isophorone diisocyanate (from isophoronediamine) and naphthyl diisocyanate (from naphthyldiamine), more preferably of methylene diphenylene diisocyanate, mixtures of methylene diphenylene diisocyanate and polymethylene polyphenylene polyisocyanate, and tolylene diisocyanate. The method of the invention is most preferably suitable for preparation of methylene diphenylene diisocyanate and mixtures of methylene diphenylene diisocyanate and polymethylene polyphenylene polyisocyanate.

The reaction of the H-functional reactant with phosgene in the reaction section (1000) from A) in regular operation, depending on the H-functional reactant to be converted, can be effected in the gas or liquid phase.

In the case of liquid phase reactions, it is customary and also envisaged in the method of the invention to dissolve the H-functional reactant (2) and/or phosgene (3) in an organic solvent (4), then to mix (A.I)) and subsequently to react (A.II)) the two co-reactants. It is possible here for both co-reactants to be dissolved in an organic solvent (4) or else just one, in which case the other is used either in neat form (without prior dissolution) or in aqueous solution.

In the case of gas phase reactions, it is customary and also envisaged in the method of the invention to liquefy the gaseous crude product by direct cooling (i.e. with physical contact with a cooling medium) or indirect cooling (i.e. without physical contact with a cooling medium) to such an extent that the desired chemical product (1) is obtained in the liquid phase that forms (apart from possibly small fractions that remain in the gas phase at first and are recovered by downstream workup steps). Suitable cooling media are especially an organic solvent (4), recycled and cooled chemical product (1), or a mixture of the two. In this way, in gas phase reactions too, a liquid phase (60) comprising the chemical product (1) is obtained.

The reaction of alcohols (2) with phosgene (3) to give (poly)carbonates (1) is effected in the liquid phase, preferably as an interfacial polycondensation. The alcohol (2) is reacted here in an aqueous solution of a base (preferably alkali metal hydroxide, especially sodium hydroxide), i.e. in the form of an alkoxide, with phosgene (3) dissolved in an organic solvent (4) (preferably an aliphatic hydrocarbon having halogen substitution, especially mono-, di- or trichloromethane or tetrachloroethylene). The (poly)carbonate (1) formed is transferred into the organic phase; the hydrogen chloride released is transferred into the aqueous phase (61) in the form of the corresponding salt. In this method version, mixing zone (1100) and reaction zone (1200) should not be separated strictly from one another; the entire mixing and reaction apparatus used should therefore be regarded as one plant component (1100-1200). Excess phosgene (3) remains partly dissolved in the liquid phase (60) and is partly transferred into the gas space via the liquid reaction mixture (into the phosgene-containing process offgas stream (70)). The (organic) liquid phase (60) containing the (poly)carbonate (1) and the aqueous liquid phase (61) comprising the hydrogen chloride released in the form of the salt of the base used are separated from one another. At least the liquid phase (60) is worked up in B).

In one embodiment of the invention, the reaction of organic primary amines with phosgene to give isocyanates is effected in the liquid phase. Amine (2) and phosgene (3) are dissolved here in an organic solvent (4), and the solutions thus obtained are mixed and reacted. Mixing in the mixing zone (1100) can be accomplished using either (i) static mixing units (preferably nozzles) or (ii) dynamic mixing units (preferably rotor-stator mixers). In the former case (i) mixing zone and reaction zone are preferably disposed in a single apparatus (a single plant component 1100-1200), for example in that a nozzle tube (optionally even multiple nozzle tubes) for supply of one of the starting materials projects into a tubular reactor which surrounds this nozzle tube (optionally the multiple nozzle tubes) and through which the other starting material flows. In the latter case (ii), mixing zone and reaction zone are preferably disposed in two apparatuses: in a dynamic mixer (1100) with downstream dwell time reactor (1200). However, other configurations of case (ii) (e.g. dynamic mixing unit and dwell zone in one apparatus) are not ruled out. In any case, at the end of the continuous flow reaction zone (1200), a liquid phase (60) comprising the isocyanate (1) (and solvent (4) and fractions of dissolved phosgene and hydrogen chloride) and a phosgene-containing process offgas stream (70) (which, in this embodiment, also contains hydrogen chloride) are obtained, both of which are worked up in B).

In another embodiment of the invention, the reaction of organic primary amines with phosgene to give isocyanates is effected in the gas phase Amine (2) and phosgene (3) are transferred into the gas phase, mixed and reacted (still in the gaseous state). The mixing is effected here preferably by means of nozzles as described above for the liquid phase reaction. Mixing zone and reaction zone are then disposed in a single mixer-reactor (1100-1200). The crude gaseous process product obtained is cooled rapidly by contacting with a quench liquid (solvent (4) and/or recycled isocyanate) at a temperature below the boiling point of the isocyanate (1) and above the decomposition point of the corresponding carbamoyl chloride, with transfer of the isocyanate formed to the liquid phase that forms. In this way, a liquid phase (60) comprising the isocyanate (1) (and the quench liquid used and fractions of dissolved phosgene and hydrogen chloride) and a phosgene-containing process offgas stream (70) (which, in this embodiment, also contains hydrogen chloride) are obtained, both of which are worked up in B).

In all embodiments of the invention in which an organic solvent (4) is used, this is preferably selected from the group consisting of aliphatic hydrocarbons having no halogen substitution [preferably decahydronaphthalene], aliphatic hydrocarbons having halogen substitution [preferably mono-, di- or trichloromethane or tetrachloroethylene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents. For the production of. Preference is given to using monochlorobenzene (MCB) or ortho-dichlorobenzene (ODB).

The workup of the liquid phase (60) obtained in A.II) comprising the chemical product (1) and of the gas phase obtained in A.II) comprising phosgene in regular operation, depending on the H-functional reactant to be converted and the procedure in A), can be implemented in various ways, but in any case includes the separation of gaseous phosgene from the liquid phase (60) in the separation unit (2100-2500). Suitable devices for the purpose are familiar to the person skilled in the art; preference is given to using a distillation column or an arrangement of multiple distillation columns for this purpose. A liquid phase (100) depleted of phosgene and containing the chemical product (1) is obtained here, as well as a process offgas stream (170) containing the phosgene removed. The phosgene-containing process offgas stream (170) thus obtained, optionally after passing through further workup steps, is sent to the first phosgene breakdown unit (3011), the mode of operation of which is elucidated further down.

Such an optionally performed further workup step especially includes a separation of hydrogen chloride from the phosgene-containing process offgas stream (170) in the plant component B.II) already mentioned further up, the separation unit (2600). This embodiment is performed when the liquid phase (60) comprising the chemical product (1) contains significant proportions of hydrogen chloride, which is regularly the case when the reaction in A) takes place in the absence of an aqueous medium without neutralization of the hydrogen chloride formed, which is the case especially in the preparation of isocyanates. In that case, the phosgene-containing process offgas stream (70) obtained in A.II) also contains considerable proportions of hydrogen chloride, which is appropriately likewise removed in the separation unit (2600). Suitable methods of removing hydrogen chloride from gaseous streams are known to the person skilled in the art and can also be used in the context of the present invention. Examples include the absorption of the hydrogen chloride in water or dilute hydrochloric acid (hydrochloric acid at a concentration in the range from 0.50% by mass to 15.0% by mass). Regardless of the exact procedure, a phosgene-containing process offgas stream (200) depleted of hydrogen chloride and a hydrogen chloride-containing (or hydrochloric acid-containing in the case of absorption in aqueous medium) stream (190) are obtained in B.II.

In preferred embodiments of the invention, the liquid phase (100) depleted of phosgene and containing the chemical product (1) is purified in B.III), a purifying unit (2400), in order to obtain the chemical product (1) to be prepared in a form of maximum purity. The purifying unit (2400) preferably comprises a distillation column or an arrangement of multiple distillation columns connected in series.

The workup of the process offgas stream (170) or (200) obtained in B.I) or B.II) in the workup section (3000) from C) in regular operation comprises at least one stage of phosgene breakdown. According to the invention, the process offgas streams are guided into the first phosgene breakdown unit (3011). This is preferably operated in such a way that phosgene is broken down catalytically, preferably over activated carbon, using an aqueous stream at a temperature in the range from 5.0° C. to 50.0° C., preferably 20.0° C. to 40.0° C. The aqueous stream may be water, especially service water, steam condensate (i.e. condensed steam obtained in condensers, such as heat exchangers in particular), demineralized water or a mixture of at least two of these. It is likewise possible to use 1% to 3% hydrochloric acid (percentages based on the total mass of the hydrochloric acid) as the aqueous stream. One option here is to recycle the aqueous stream obtained in the phosgene breakdown unit—containing hydrochloric acid owing to the hydrolysis of phosgene, in which case a portion of the aqueous stream containing hydrochloric acid can be discharged in order to avoid excessively high concentration. The use of steam condensate is preferred, especially in conjunction with recycled stream containing hydrochloric acid from the phosgene breakdown unit. The phosgene is broken down at a pressure in the range from 800 mbar to 1000 mbar (absolute), preferably 850 mbar to 950 mbar (absolute), which is preferably brought about by means of a ventilator mounted beyond the phosgene breakdown unit (3011). The first phosgene breakdown unit (3011) may comprise multiple plant components, especially multiple, especially two, tubular reactors connected in series, called "phosgene destruction towers". It is possible here for a ventilator present with preference to be mounted beyond each plant component for phosgene breakdown or else solely beyond the last plant component for phosgene breakdown in flow direction.

When the process offgas guided into the workup section (3000) still contains substantial proportions of solvent (4), it may be appropriate to adsorb and hence to remove this solvent in a solvent adsorption downstream of the phosgene breakdown (not shown in the drawings).

According to the invention, the workup section (3000) from C) comprises at least one first phosgene breakdown unit (3011) for process offgas streams and at least one second phosgene breakdown unit (3012) for oxygen-containing offgas streams. The at least one second phosgene breakdown unit (3012) for oxygen-containing offgas streams is preferably constructed and is preferably operated as described above for the at least one first phosgene breakdown unit (3011) for process offgas. The at least one second phosgene breakdown unit (3012) is not necessarily required in regular operation, but it is appropriate in many cases to keep it in operation even during regular operation.

What this enables is firstly disposal of oxygen-containing gas streams (410-X) from sampling points via units provided specifically for that purpose. These units for removing oxygen-containing offgas streams from sampling points may be permanently mounted conduits (in the form of fixed piping) or flexibly mountable devices such as hoses made of plastic (preferably polyethylene), rubber or especially metal; in each case (no matter whether in the form of fixed piping or flexible), it is preferable to manufacture the units for removing oxygen-containing offgas streams from an electrically conductive material. Irrespective of that, it is secondly possible in principle to keep conduits ready in the form of fixed piping from all phosgene-conducting plant components into the at least one second phosgene breakdown unit (3012), through which, in the event of an emergency shutdown of a plant component in the case of a leak, oxygen-containing offgas can be sent to the phosgene breakdown without first having to establish the prerequisites for this in a time-consuming manner.

The incineration of the worked-up process offgas (210) obtained in C) in the incineration unit (6000) from D) can in principle be effected as known from the prior art.

For safety reasons, in all embodiments of the invention, it is preferable to prepare the phosgene (3) required for the performance of the reaction in A) in situ by reaction of carbon monoxide (300) with chlorine (310) in a phosgene preparation section (0) comprising an apparatus (4000) for phosgene preparation. For the execution of this step, it is possible to utilize a "low-temperature combiner" according to EP 1 640 341 B1 or a "high-temperature combiner" according to EP 0 134 506 B1. Each method gives rise to a process offgas stream (320) comprising carbon monoxide and residues of phosgene, which, especially after passing through further purification steps, is preferably sent to the first phosgene breakdown unit (3011). In all embodiments of the invention, it is preferable, in the event of a production stoppage, to shut down the further preparation of phosgene, optionally with a time delay after shutdown of the supply of the H-functional reactant (2) in order to avoid the formation of large amounts of phosgene that would have to be stored intermediately until production is restarted.

In the method of the invention, individual plant components can be operated in regular operation and in circulation mode at a reduced pressure relative to ambient pressure. This especially relates to the plant components of the workup section (2000) from B). The vacuum generation plants required for the purpose produce process offgas streams (not shown in the drawings). These process offgas streams (optionally after passing through further purification steps such as the removal of entrained solvent (4); a removal of hydrogen chloride will generally not be required and is therefore preferably omitted) are likewise fed to the first phosgene breakdown unit (3011) by condensation or droplet formation.

In a preferred embodiment, the offgas from the vacuum system is sent to a dedicated phosgene breakdown unit provided for the vacuum system only. In such a case, the first phosgene breakdown unit (3011) consists of at least two separately operated phosgene breakdown plant components (3011-1, 3011-2). These phosgene breakdown plant components (3011-1, 3011-2) are set up and operated as described above for the first phosgene breakdown unit (3011). During the preparation of the chemical product (1) in regular operation, one of these two phosgene breakdown plant components (3011-1) is supplied solely with the process offgas streams from the vacuum generation plants, while the other phosgene breakdown plant component (3011-2) is supplied with all other process offgas streams. If there is a leak or a similarly serious problem in the vacuum generation plants, these are shut down, but remain connected to the phosgene breakdown plant component (3011-1) assigned thereto, such that all the offgas streams obtained therein, whether they contain oxygen or not, are fed into a dedicated phosgene breakdown separate from all other offgas streams. The other plant components of the production plant can then be put in circulation mode in the manner described. In this case, the phosgene breakdown plant component (3011-1) fulfills the same function as the second phosgene breakdown unit (3012) in all other cases.

Figure 2:
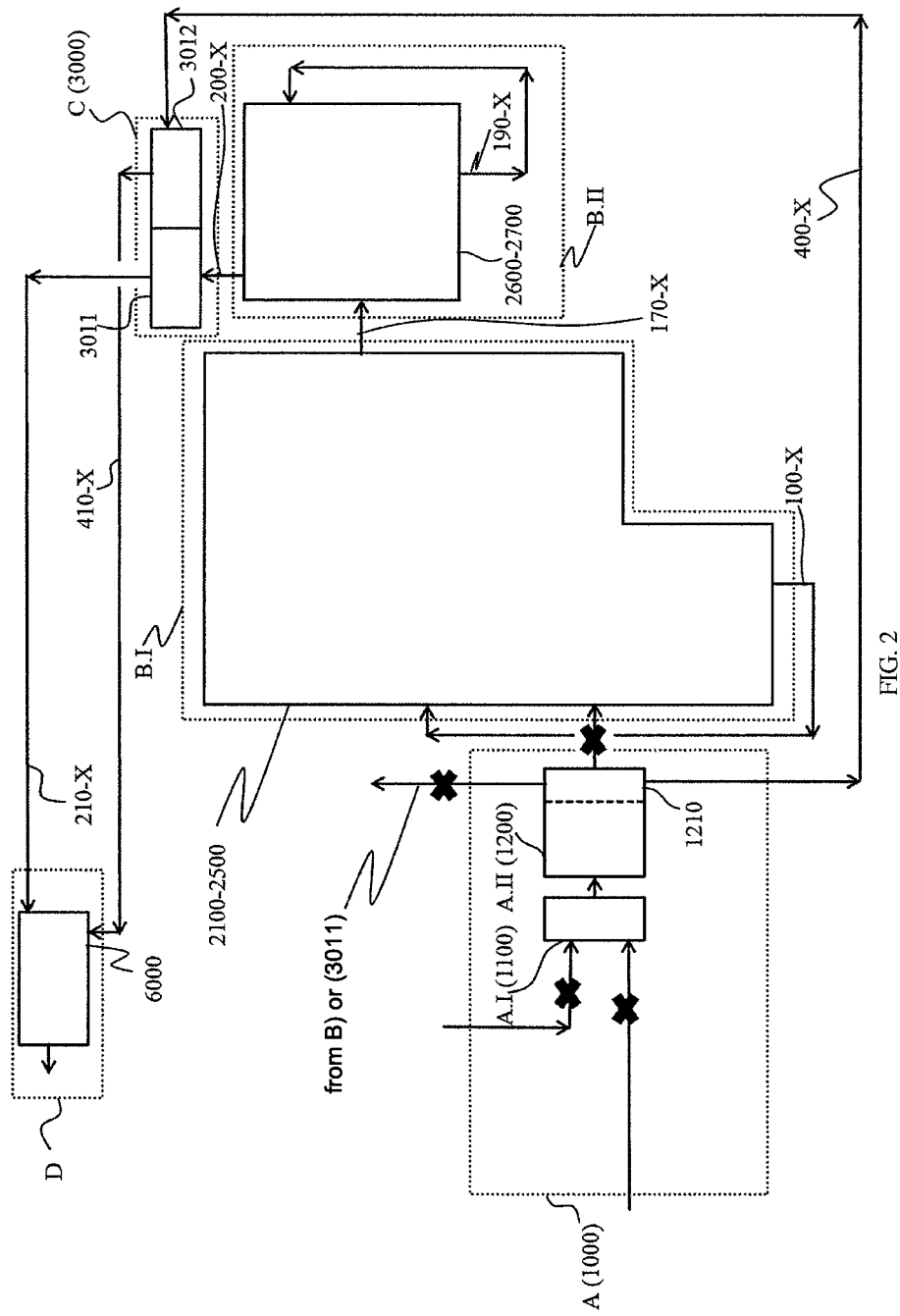
FIG. 2 is a schematic illustration of an embodiment of the method of the invention in the event of a production stoppage using the example of the shutdown of the entire reaction section (1000) from A)

The procedure of the invention in the event of a production stoppage is shown in FIG. 2 using the example of the shutdown of the entire reaction section (1000) from A):

The conduits for the supply and removal of the reactants and products in regular operation are closed (shown by an "x" in the corresponding conduits). Oxygen-containing offgas (400-X) from the reaction zone (1200) or from a separation zone (1210) integrated into the reaction zone is supplied via a unit specially provided for the purpose to the second phosgene breakdown unit (3012). This unit for removing the oxygen-containing offgas (400-X) may be a permanently mounted conduit (in the form of fixed piping). However, it is likewise possible for this purpose to use a flexibly mountable device such as a hose made of plastic (preferably polyethylene), rubber or especially metal; in any case (whether in the form of fixed piping or flexible), it is preferable to manufacture the devices for removing oxygen-containing offgas from an electrically conductive material. This circulation mode is implemented in the embodiment according to FIG. 2 in that the liquid output streams (100-X) from B.I) and (190-X) from B.II) are recycled into the respective plant component (the suffix "-X" indicates that the streams have a different composition than the corresponding streams in regular operation, (100) and (190)). The gas pathway from B.I) to B.II) is open (via stream (170-X)). The gas pathway from B.II) to C) is likewise open, meaning that process offgas (200-X) gets into the first phosgene breakdown unit (3011). The process offgas stream (210-X) that has been freed of phosgene and is obtained in the first phosgene breakdown unit (3011) and the process offgas stream (410-X) that has been freed of phosgene and is obtained in the second phosgene breakdown unit (3012) are supplied via separate conduits to spatially separate points in the incineration unit (6000) from D) and incinerated therein.

For better understanding of the procedure of the invention in the event of production stoppages, particularly preferred embodiments of the regular operation of the preparation of isocyanates (1), which are more preferably chemical products (1) in the context of the invention, are described in detail hereinafter (cf. FIG. 3).

The continuous or semicontinuous, preferably continuous, production of the isocyanate in the reaction section (1000) from A) can be effected by one of the methods known from the prior art. Suitable processes are described, for example, in EP 2 077 150 A1, EP 1 616 857 A1, EP 1 873 142 A1, EP 0 716 079 A1 and EP 0 314 985 B1 (liquid phase processes), and EP 2 196 455 A1, EP 1 449 826 A1 and WO 2015/144681 A1 (gas phase processes). However, concentrations and flow rates of the amine (2) and phosgene (3) reactants are preferably chosen such that a molar ratio of phosgene to primary amino groups of 1.1:1 to 30:1, more preferably of 1.25:1 to 3:1, is established in the mixing of the co-reactants in A.I).

In a preferred embodiment of the method of the invention, amine (2) and phosgene (3) from corresponding reservoir vessels (1020, 1030) are sent to the mixing in (1100). This is preferably done in the form of solutions (20, 30) in the solvent (4). In the case of gas phase processes, it is possible to dispense with the dissolution of the reactants in solvent (4).

Phosgene (3) is prepared by reacting carbon monoxide (300) with chlorine (310) in the apparatus (4000)—called "phosgene combiner". What is obtained here is a process offgas stream (320) comprising carbon monoxide and residues of phosgene, which, especially after passing through further cleaning steps, is preferably sent to the first phosgene breakdown unit (3011). Suitable cleaning steps include an absorption of the process offgas stream (320) in solvent (4) having a temperature in the range from 0.0° C. to −20.0° C. in an absorption column ("phosgene scrubber"; (4010)), wherein some of the phosgene is scrubbed out of the process offgas stream (320) comprising carbon monoxide and residues of phosgene. The scrubbed process offgas stream (330) thus obtained is sent to the first phosgene breakdown unit (3011), preferably as shown in FIG. 3 by mixing with stream (200).

Suitable units for the configuration of the mixing zone (1100) are sufficiently well known from the prior art and have already been described further up by way of example. After the mixing, the reaction mixture (50) is guided into the reaction zone (1200). This is a dwell time unit in which the mixture obtained in the mixing zone (1100) is given sufficient opportunity to react to completion. Suitable apparatuses are sufficiently well known from the prior art. The separation of the crude process product into the liquid phase (60) and the phosgene-containing process offgas stream (70) is effected in the actual reaction zone itself or in a separation zone (1210) that should be regarded as part of A.II). It is also possible to integrate the mixing zone and reaction zone or the mixing zone, reaction zone and separation zone or the reaction zone and separation zone into a single apparatus (for example into a corresponding reactor). According to the invention, it is also possible for multiple mixing zones and/or reaction zones and/or, if present, separator zones to be connected in series or in parallel; for example in the form of a cascade of multiple series-connected reactors. The process product obtained in the reaction zone (1200) separates into a liquid phase (60) comprising, as well as the desired isocyanate, dissolved hydrogen chloride, excess dissolved phosgene and solvent, and a gaseous process offgas stream (70) further comprising hydrogen chloride gas and gaseous solvent. The reaction zone may be followed, if required, by an apparatus for cleaving carbamoyl chloride (not shown in FIG. 3). In such a case, the liquid phase (60) passes through this apparatus before it is subjected to the workup in the workup section (2000) from B). The resultant hydrogen chloride-enriched gas phase is preferably combined with the phosgene-containing process offgas stream (70) and they are subjected to further workup together.

This workup in workup section (2000) from B) firstly comprises a step of depleting phosgene and hydrogen chloride from liquid phase (60) from A.I) by separating this liquid stream (60) into a liquid stream (80) comprising solvent and isocyanate, and a gaseous process offgas stream (90) comprising phosgene and hydrogen chloride in a distillation apparatus (2100; "dephosgenation column"). This "dephosgenation column" can be operated by any method known from the prior art, preferably as described in EP 1 854 783 B1, especially in paragraphs [0018] and [0023].

The liquid stream (80) thus obtained is separated in a distillation apparatus (2200; "solvent column") into a process offgas stream (110) still containing solvent and a liquid stream (100) containing isocyanate. This can be effected by any method known from the prior art, preferably as described in EP 1 854 783 B1, especially in paragraphs [0024] to [0027]. The distillation apparatus (2200) may also comprise two or more distillation columns connected in series (this option is not shown in FIG. 3 for reasons of simplification of the drawing).

The process offgas stream (110), preferably after liquefaction in a condenser (2310), is separated in a distillation apparatus (2300; "solvent stripper") into a liquid stream (120) containing solvent and a gaseous phosgene-containing process offgas stream (130). This can be effected by any method known from the prior art, preferably as described in EP 1 854 783 B1, especially in paragraphs [0027] and [0028].

The phosgene-containing process offgas streams (70), (90) and (130) thus obtained are cleaned (i.e. freed of the majority of the phosgene) in an absorption apparatus (2500; "phosgene absorber") by absorption in solvent (4) to obtain a liquid stream (160) comprising solvent and phosgene and a gaseous process offgas stream (170) comprising hydrogen chloride and solvent, wherein the gaseous phosgene-containing process offgas streams (70) and (90) are preferably first combined and the combined phosgene-containing process offgas stream from (70) and (90) and the phosgene-containing process offgas stream (130) are each condensed and then introduced in liquid form into the absorption apparatus (2500). This cleaning can be effected by any process known from the prior art, preferably as described in EP 2 093 215 A1. The phosgene-laden solvent stream (340) obtained in the phosgene scrubber (4010) is appropriately likewise sent to the absorption apparatus (2500).

In the embodiment described, the units (2100), (2200), (2300) and (2500) constitute individual plant (sub-)components of the (overall) plant component (2100-2500) from B.I).

The phosgene-containing process offgas stream (170) obtained in this way contains the hydrogen chloride formed in the reaction and is therefore sent to the hydrogen chloride removal in the removal unit (2600). This depletion of the hydrogen chloride content from B.II) is preferably effected by absorption of hydrogen chloride in water or dilute hydrochloric acid as absorbent (180) in a further absorption apparatus (2600; "HCl absorption column") to obtain a hydrochloric acid-containing stream (190) and, preferably after passing through a vapor condenser (2630), a gaseous phosgene-containing process offgas stream (200) comprising solvent and optionally gaseous secondary components. This step can be effected by any method known from the prior art. Preference is given to procedures as described in EP 2 021 275 B1.

The absorbent (180) used is water (e.g. steam condensate) or hydrochloric acid in a concentration in the range from 0.50% by mass to 15.0% by mass (dilute hydrochloric acid). The hydrochloric acid-containing stream (190) is discharged into the hydrochloric acid tank (2610). As well as the hydrochloric acid tank (2610), a further storage tank (2640) is disposed such that it can accept stream (190) if required. This "dilute acid tank" (2620) is utilized when the composition of the stream (190) differs significantly from the specification required for hydrochloric acid, which occurs in the event of a production stoppage.

The heat released in the absorption of the hydrogen chloride transfers solvent present in stream (170) predominantly or completely to the gas stream (200).

In the preferred embodiment using the vapor condenser (2630), a liquid stream (191) is obtained therein. The stream (191) generally contains aqueous and organic constituents. In this embodiment, it may therefore be appropriate to separate stream (191) in a phase separation apparatus (2640) into an aqueous phase (192) and an organic phase (193). The aqueous phase (192) is preferably—especially preferably after discharge into the dilute acid tank (2620)—recycled into the HCl absorption column (2600) as a constituent of the absorbent (180). The water-saturated organic phase (193), for further use, is collected in a receiver vessel (2650) and, preferably after drying (especially by means of molecular sieves in a drying vessel 2660), is recycled, preferably into the distillation column (2200), for example by mixing the organic phase with the stream (80) or, as shown in FIG. 3, introduced into this distillation column independently of stream (80).

For preparation of the desired isocyanate (1) in pure form, it is preferable to further distill the liquid phase (100) obtained in the above-described solvent column (2200) in a distillation unit (2400) (B.III) after removal of the solvent. A liquid isocyanate stream (140) is obtained here from the liquid phase (100), giving a gaseous stream (150) containing secondary components, with or without solvent. Optionally, B.III) comprises the removal of polymeric isocyanate fractions in an upstream unit for polymer removal (2410) as stream (141). The purification of the liquid phase (100) by distillation can be effected by any method known from the prior art. Suitable methods are described in EP1475367B1, or else in EP 1 371 635 B1.

In this embodiment, the stream (140) thus comprises the isocyanate (1) in a purified form. In this context, (140) may also cumulatively represent different isocyanate streams (1) of different isomer composition (140-1, 140-2, . . . ), if the distillation in 2400 includes not just a cleaning operation but also an isomer separation. In addition, the stream 141 obtained in particular embodiments also contains isocyanates (1), where stream 141 comprises, in particular, polymeric isocyanate fractions (i.e. isocyanates (1) that can be derived from polymerized amines, for example polymethylene polyphenylene polyisocyanates having three or more benzene "nuclei"). The "residue stream" 143 obtained in the particular embodiments—i.e. particularly without the upstream polymer removal in 2410—also still contains isocyanate (1), which can be obtained from this stream. The latter embodiment is particularly suitable for the preparation of tolylene diisocyanate, in which case the distillation apparatus 2400 is preferably configured as a dividing wall column.

The distillation apparatuses (2200), (2300) and, if present, (2410) and (2400) are preferably operated under reduced pressure compared to ambient pressure. The process offgas streams formed here, optionally after a removal of solvent by condensation or droplet separation, are sent to the first phosgene breakdown unit (3011).

The phosgene-containing process offgas stream (200) obtained in this way is sent to the first phosgene breakdown unit (3011) from C). Phosgene is broken down here catalytically, preferably over activated carbon, using an aqueous stream (260) to obtain a gaseous stream optionally containing solvent and optionally containing gaseous secondary components and a liquid hydrochloric acid stream which is partly discharged into the tank for dilute hydrochloric acid (2620) and partly recycled and used as a constituent of the aqueous stream (260). Preferably, the process offgas and the aqueous stream (260) are conducted through the activated carbon bed in cocurrent. The gaseous stream optionally passes through an adsorption apparatus (3020) for adsorption of solvent (not shown in FIG. 3) to obtain the process offgas stream (210).

The process offgas stream (210) that has been freed of phosgene and is obtained in this way is sent to the incineration unit (6000) from D).

Figure 3:
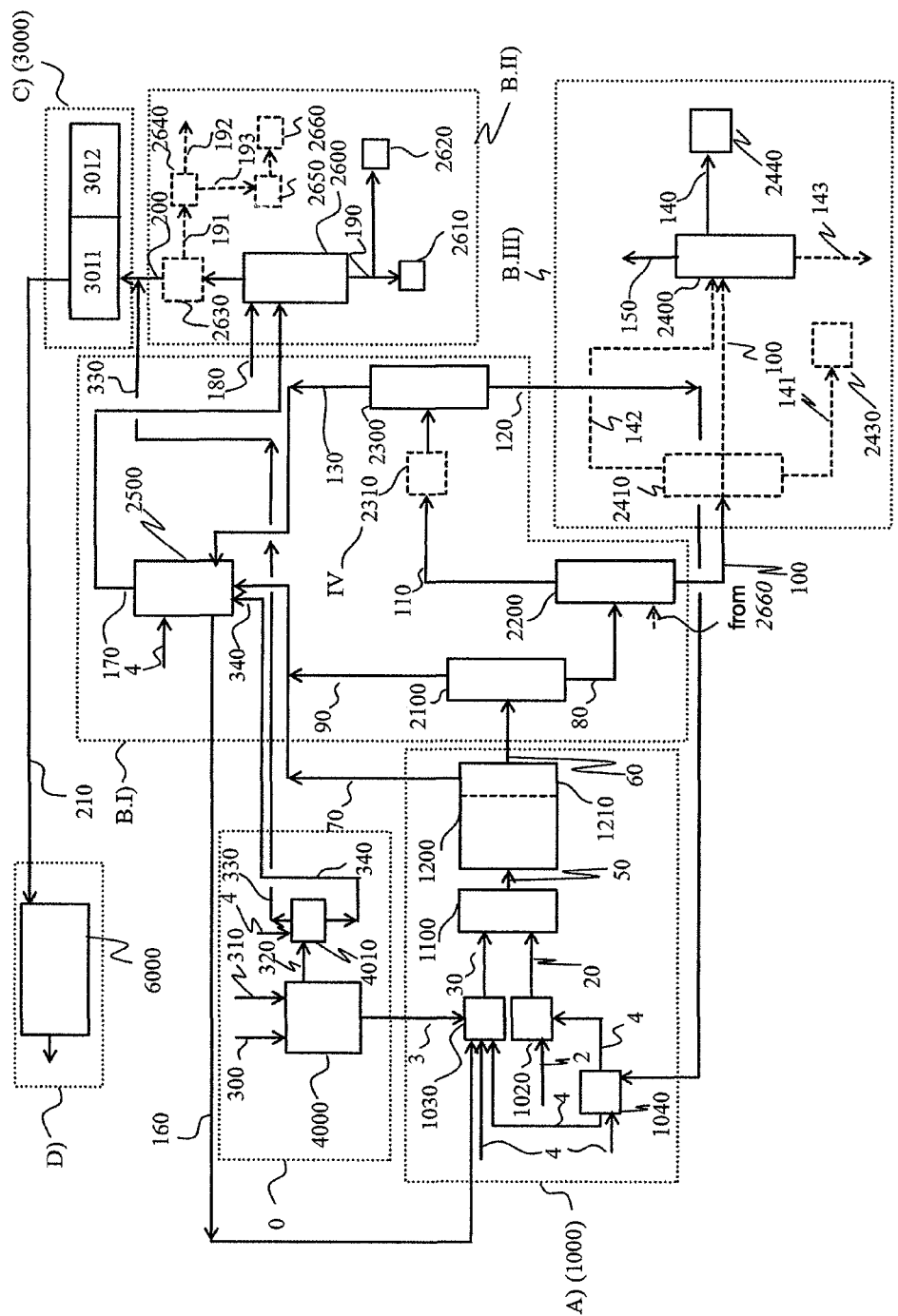
FIG. 3 is a schematic illustration of an embodiment of the method of the invention in the event of production stoppages, in the case of the regular operation of the preparation of isocyanates.
Figure 4A:
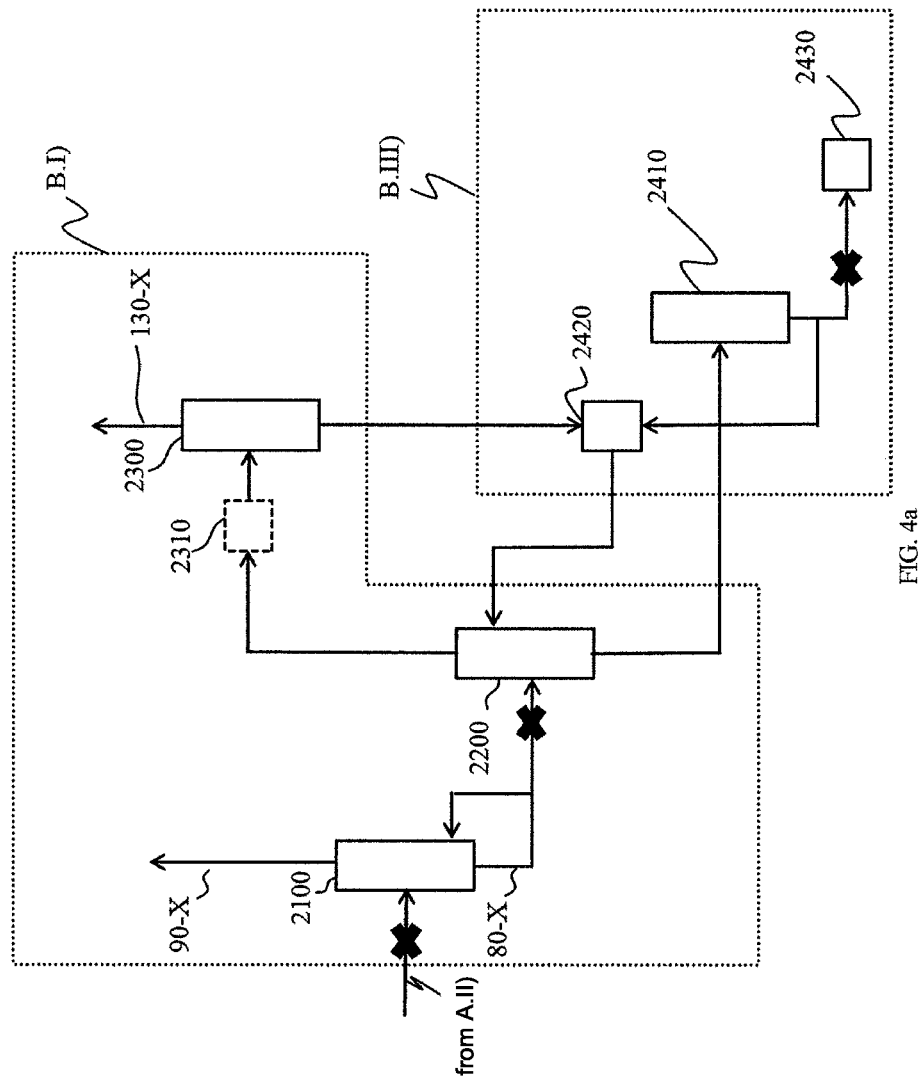
FIGS. 4a-4b are schematic illustrations of embodiments of the circulation mode of the invention in the process shown in FIG. 3 in the event of a stoppage of isocyanate production.
Figure 4B:
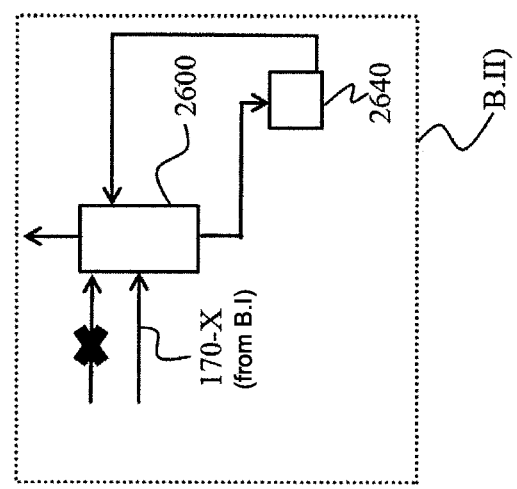

Preferred embodiments of the circulation mode of the invention in the process shown in FIG. 3 in the event of a stoppage of isocyanate production are shown in FIGS. 4a-b:

A first circulation mode is established in that the distillate from the distillation apparatus (2200) consisting predominantly of solvent (4) is run into the distillation apparatus (2300). The bottoms from the solvent purification (2300) are cooled (not shown in the figures) and run into a storage tank (2420) (the "crude MDI storage tank"; cf. FIG. 4a, not shown in FIG. 3). Operation of the solvent purification in the distillation apparatus (2300) is continued here. The crude isocyanate from the crude MDI storage tank (2420), becoming diluted with solvent, is run therefrom by means of the discharge pump back into the solvent distillation (2200) and hence a circulation mode (2200) (2300) (2200) is established.

A second circulation mode is established in that the crude isocyanate solution from the solvent distillation (2200) is run via the unit for removal of polymeric isocyanate fractions (2410), especially in cold form (i.e. with the column bottoms heating (2410) switched off) into the crude MDI storage tank (2420) and thence back into the solvent distillation (2200), and hence a circulation mode (2200) (2410) (2200) is established; cf. likewise FIG. 4a. Provided that the solvent purification (2300) is in operation, the distillate therefrom (130-X; solvent (4) with traces of phosgene (3)) is pumped into and collected in the phosgene absorber (2500). If required, excessively large volumes are guided from the phosgene absorber (2500) into the phosgene dissolution vessel (1030). The first and second circulation mode have the common feature of the conduit from the storage tank (2420) into the distillation apparatus (2200).

A third circulation mode is established in that the liquid phase (80-X) comprising crude isocyanate solution which is withdrawn from the dephosgenation column (2100) is pumped in circulation back into the column; cf. likewise FIG. 4a. This is preferably accomplished by means of a steam-heated circulation evaporator (not shown in FIG. 4a).

A fourth circulation mode is established in that the outflow from hydrogen chloride absorption (2600) is switched from the hydrochloric acid tank (2630) to the weak hydrochloric acid tank (2640). The weak hydrochloric acid is run from there back to the top of the absorber of the hydrogen chloride absorption and in this way a circulation mode (2600) (2640) (2600) is established; cf. FIG. 4b. The supply of further absorbent (180) is stopped here (shown by the "x" in the corresponding conduit), and the offgas pathway from B.I) via B.II) into the phosgene breakdown from C) remains open.

If all aforementioned circulation modes are established, the gaseous exit streams from the dephosgenation (90-X) and the solvent distillation (130-X) flow through the phosgene absorption (B.I), 2500) and thence as stream (170-X) into the hydrogen chloride absorption (B.II), 2600). The phosgene absorption (B.I), 2500) preferably remains in regular operation here at its customary operating pressure and the customary operating temperatures; only the feeding of solvent (4) is stopped.

The aforementioned circulation modes one to four are particularly suitable when, as shown in FIG. 2, the reaction section (1000) from A) is to be shut down.

The invention relates to the case that the production of the chemical product has to be shut down since a measure associated at least temporarily with the occurrence of oxygen-containing offgas (400-X) has to be implemented in a plant component. Oxygen can penetrate, for example, when a plant component that has been shut down has to be opened or a leak has occurred in a plant component. According to the invention, the resultant oxygen-rich offgas streams (400-X) are sent to the at least one second phosgene breakdown unit (3012). Their mode of operation can in principle be effected as described above for the first phosgene breakdown unit (3011), to which reference is made here. The phosgene breakdown unit (3012) preferably comprises one or more (3012-1, 3012-2, . . . ) phosgene breakdown plant components (phosgene breakdown reactors, called phosgene destruction towers) that are filled with activated carbon (e.g. Norit RB4C) and are operated at reduced pressure relative to ambient pressure, especially at one pressure (see the description of the first phosgene breakdown unit (3011)). The phosgene breakdown unit (3012) here may also comprise multiple, especially two, phosgene breakdown plant components (3012-1, 3012-2) that are connected in parallel. These phosgene breakdown plant components (3012-1, 3012-2) are fed with oxygen-rich offgas from various sources (for example, a phosgene breakdown plant component (3012-1) may be kept ready for oxygen-rich offgas (410-X) that occurs in regular operation and is especially obtained in the event of sampling for analytical purposes, are another phosgene breakdown plant component (3012-2) is kept ready only for oxygen-rich offgas (400-X) obtained in the event of a measure). The phosgene breakdown plant components here are constructed and operated as described above. These may, for example, be tubular reactors.

The invention further relates to a production plant for preparation of a chemical product (1) by reacting an H-functional reactant (2) with phosgene (3), which is configured as already described above and is suitable for operation by the method of the invention. All the preferred configurations described above in connection with the method of the invention, especially those that relate to preferred apparatus-related configurations, are of course also applicable to the production plant of the invention.

The method of the invention gives rise at least to the following advantages:
I) minimization of safety-related devices and apparatus-related demands through reliable compliance with explosion limits;
II) the controlled supply of oxygen-rich offgas to the incineration unit without the need for excessive dilution with inert gases reduces or avoids the feeding of natural gas into the incineration unit during a production stoppage;
III) reduction of the time taken for repairs and maintenance measures since the installation of a nitrogen supply for inertization of the region affected is dispensed with;
IV) avoidance of escape of environmental pollutants on sampling;
V) avoidance of deposits that can result from reactions of the chemical product with oxygen and/or moisture on combination of process offgas and oxygen-rich offgas (for example urea formation in the case of isocyanates);
VI) avoidance of corrosion damage in the production plant because contact of hydrogen chloride and/or phosgene with moisture is reduced;
VII) minimization of the consumption of inert gases such as nitrogen because, in the case of separate conduction of low-oxygen and oxygen-rich offgas, there is no need to keep the entirety of the offgas outside the explosion range by dilution with inert gases; and as a result
VIII) reduction in natural gas consumption in the incineration unit;
IX) reduction in the time taken for a repair or maintenance measure.

The success of the procedure of the invention for separate processing of the oxygen-rich offgas by use of a second phosgene breakdown unit compared to the utilization of the existing phosgene breakdown unit in the preparation of chemical products by reaction of phosgene with H-functional reactants was surprising to the person skilled in the art. The at least one second phosgene breakdown unit for oxygen-rich offgas enables distinct shortening of repair and maintenance operations and also leads to an improvement in sampling for analytical purposes from the aspects of occupational safety and the environment. The unavoidably higher capital costs associated with the procedure of the invention are rapidly compensated for as a result, which was not to be expected by the person skilled in the art. The additional maintenance expenditure is low (for instance, an exchange of the activated carbon used with preference in the second phosgene breakdown unit is generally required only once every five years).

The invention is elucidated in more detail by the examples.

EXAMPLES

A. General Conditions

A.I General Conditions for the Preparation of a Mixture of Methylene Diphenylene Diisocyanate and Polymethylene Polyphenylene Polyisocyanate (Collectively MDI) by Phosgenation of a Mixture of Methylene Diphenylene Diamine and Polymethylene Polyphenylene Polyamine (Collectively MDA) in Regular Operation—Cf. Also FIG. 3

The procedure is in principle as described in WO 2017/050776 A1 (pages 35 and 36), with the following differences or further details of the method regime that are not mentioned explicitly in WO 2017/050776 A1:
20.4 t/h of MDA as starting material are mixed in 55.0 t/h of monochlorobenzene (MCB) to give a 27.1% MDA solution.
100 t of phosgene solution per hour are mixed with the MDA solution.
The bottom product (100) obtained is 25.45 t/h of MDI.
The hydrogen chloride absorption (method stage B.II); method stage VII in WO 2017/050776 A1) is operated with the additional units (2630), (2640), (2650) and (2660) elucidated above in connection with FIG. 3.
The phosgene breakdown unit consists of two phosgene destruction towers connected in series, each filled with 14 $m^3$ of activated carbon (Norit RB4C), that are operated at a reduced pressure of 930 mbar (absolute) and in which phosgene is broken down by reaction with water (water condensation and dilute hydrochloric acid). Between the phosgene breakdown unit (3011) and the offgas incineration (6000) there is a solvent adsorption stage (3021; not shown in FIG. 3) as a further constituent of the offgas workup (C, 3000) in which residual solvent (4) is removed from the process offgas stream by adsorption on activated carbon.
Offgases are sucked into the offgas workup by means of ventilators that generates a reduced pressure of 930 mbar (absolute). Such ventilators are beyond the phosgene breakdown and beyond the solvent adsorption.

A.II. General Conditions for the Preparation of Phosgene (Process Stage 0)—Cf. Also FIG. 3

The procedure is in principle as described in WO 2017/050776 A1 (pages 36 and 37; referred to in the corresponding figure as process stage IX), with the following differences or further details of the method regime that are not mentioned explicitly in WO 2017/050776 A1:

Starting materials used are 4400 m³ (STP)/h of chlorine (310) and 4650 m³ (STP)/h of carbon monoxide (300).

The shell and tube phosgene generators each contain 10 tonnes of activated carbon (Norit RB4C).

42.0 t/h of phosgene are conducted into the phosgene dissolution tank (1030).

The top product (320) from the second phosgene liquefier, 150 m³/h of excess carbon monoxide and traces of phosgene (0.50% of the total amount of offgas), before being introduced into the offgas workup (3000), are subjected to preliminary cleaning in an absorption column ("phosgene scrubber" (4010)) which is operated with cold solvent (MCB) at −17° C., scrubbing some of the phosgene out of the gas stream. The phosgene-containing MCB solution thus obtained is sent to the phosgene absorption (2500) as liquid stream (340).

What are called ammonia screw compressors are used for refrigeration in the phosgene liquefiers. In this way, the MCB solvent that finds use in the reaction and the MCB coolant with which the coolers for the condensation of the offgas streams are supplied are cooled down to −17° C.

B. EXAMPLES

Example 1 (Comparative Example): Brief Shutdown of an MDI Production Plant Comprising a Complete Shutdown of the Production Plant (Except for the Offgas Workup (C, 3000) and the Offgas Incineration (D, 6000) and Auxiliary Systems Such as the Nitrogen Supply), Performance of a Repair Measure and Restarting of the Production Plant The production plant was operated as described under A. In a departure from FIG. 3, all of the offgases, process offgases and oxygen-rich offgases (in regular operation the latter are merely streams from sampling points that occur from time to time) were conducted through one and the same phosgene breakdown unit (3010). A leak occurred in the vapor conduit for the process offgas stream (70) from a phosgenation tower (1200) into the phosgene absorption (2500), which was fixed by proceeding as follows:

Shutdown of the Production Plant (Except for the Offgas Workup (C, 3000) and the Offgas Incineration (D, 6000) and Auxiliary Systems Such as the Nitrogen Supply)

1. The supply of MDA was stopped, which resulted directly in a drop in the temperature in the mixing unit (1100). The feeds of MCB from the tank (1040) and phosgene solution from the tank (1030) were maintained for another 3 minutes, then the two streams were likewise switched off. The reaction solution that remained in the phosgenation tower was emptied via an emergency outlet into an emergency discharge vessel (not shown in FIG. 3). The gas space in the emergency discharge vessel was connected to the phosgene absorption (B.I), 2500). The pressure in the apparatuses connected to the emergency discharge vessel fell to 980 mbar (absolute). The leak results in introduction of oxygen into the offgas which is guided through the phosgene absorption (B.I), 2500), the hydrogen chloride adsorption (B.II, 2600) into the offgas workup (C), 3000).

2. After switching off the MDA supply, the phosgene preparation (0, 4000, 4010) was stopped and all inlets and outlets into it were closed. This took 3 minutes.

3. A nitrogen conduit was run to the vapor conduit affected. The assembly took 15 minutes. The blowing-in of nitrogen reduced the oxygen content of the offgas, and the pressure rose slightly to 990 mbar (absolute).

4. The vapor conduit affected was purged with MCB with introduction of nitrogen, then adhering MCB was driven out by further introduction of nitrogen. The MCB used for purging was conducted into the emergency discharge vessel. This operation took 3 hours.

5. After the emergency shutdown of the reaction under number 1, the dephosgenation column (B.I), 2100), the phosgene absorption (B.I), 2500), the solvent distillation (B.I), 2200), the solvent purification (B.I), 2300) and the MDI distillation (B.III), 2400, 2410) were shut down, which took 10 minutes. The apparatuses mentioned were filled with solvent and MDI, except for the phosgene absorption (2500) that was filled with phosgene and MCB. The heaters of the apparatuses mentioned were switched off, such that they cooled down. The gas pathway to the phosgene absorption (B.I), 2500) remained open.

6. The hydrogen chloride absorption (B.II), 2600) remained in operation at first. The hydrogen chloride content of the gas phase (70) that was high in regular operation dropped rapidly. Within 5 minutes, the incoming amount of hydrogen chloride fell to such an extent that the hydrogen chloride absorption (B.II), 2600) formed only weak hydrochloric acid that was guided into a hydrochloric acid tank for weak hydrochloric acid (2620) that was provided for the purpose. 30 minutes after the reaction section (A), 1000) had been shut down, the hydrogen chloride absorber (2600) was shut down. The pathway to the hydrochloric acid tank (2610) was closed. The pathway to the dilute acid tank (2620) remained open. The gas pathway from the phosgene absorption (B.I), 2500) through the hydrogen chloride absorption (B.II), 2600) into the offgas workup (C), 3000) remained open. The phosgene breakdown (C, 3010) and the solvent adsorption (C), 3020) remained in operation.

7. After the hydrogen chloride absorption (B.II), 2600) had been shut down, the vacuum system of the distillation apparatuses (2200), (2300), (2410) and (2400) was shut down. Subsequently, nitrogen was added to these distillation apparatuses so as to establish ambient pressure. These operations took a total of 1 hour.

8. The refrigeration for cooling of MCB was shut down within 30 minutes.

9. The entire offgas workup (C, 3000) remained in operation. After the vacuum system had been shut down (number 7), offgas present in the phosgenation tower, in the phosgene absorption, in the hydrogen chloride absorption and in the respective gas conduits (vapor conduits) was sucked out by means of the ventilator present until a pressure of 930 mbar (absolute) was established, which took 8 hours.

Procedure for the Repair Measure

To fix the leak in the seal in the vapor conduit in question in the phosgenation tower, a seal was changed. This was done with maintenance of the reduced pressure of 930 mbar (absolute). After installation of the new seal, the vapor conduit upstream of the phosgene absorption was closed with a valve for isolation from the reduced pressure and performance of a leak test with nitrogen. Thereafter, the reaction section (A, 1000), the phosgene absorber (B.I, 2500), the hydrogen chloride absorber (B.III, 2600) and the offgas workup (C), 3000) (except for the solvent adsorption) were purged with nitrogen in order to remove the very last traces of oxygen. The time taken for the repair was 3 hours, and that for the purging with nitrogen a further 6 hours.

The change of the faulty seal took a total of 18 hours.

Restarting of the Production Plant

The procedure was as follows:

1. MCB was pumped out of the solvent tank (1040) into the emptied reaction section. After 6 hours, there was a sufficient liquid level (MCB ran out of the phosgenation tower across into the dephosgenation column). The dephosgenation column was then put into operation.
2. Refrigeration and vacuum generation were put back into operation, which took 4 hours.
3. The solvent distillation column (B.I), 2200) and the solvent purification (B.I), 2300) were put into operation successively in that sequence.
4. After starting the solvent purification (B.I), 2300), solvent from solvent tank (1040) was conducted via the reaction section (A, 1000) and the dephosgenation column (B.I), 2100) into the solvent distillation column (B.I), 2200), with the heating of the reaction zone and the dephosgenation column switched on. Then the solvent distillation was ready for operation and ran in a circuit via the solvent purification, the solvent tank, the reaction section and the dephosgenator. This operation took 8 hours.
5. With the startup of the solvent distillation and purification, a solvent-containing gaseous phase was obtained (stream 130 in regular operation), which was condensed and sent to the phosgene absorption. The phosgene-free bottom stream from the solvent purification (stream 120 in regular operation) was pumped into the solvent tank (1040). These operations took 4 hours.
6. As soon as the condensed solvent-containing gas stream arrived from the solvent purification, the cooling systems for the condensation of the process offgas streams (70) and (90) that were obtained in regular operation were made ready for use in the phosgene absorption (B.I), 2500) and the outflow of the phosgene absorption to the phosgene dissolution tank (1030) was adjusted. Subsequently, the pathway was opened from the phosgene dissolution tank (1030) to the mixing unit (1100) and the phosgenation tower (1200).
7. The phosgene production (0, 4000, 4010) was started up within 45 minutes, and the phosgene concentration in the phosgene dissolution tank (1030) was then concentrated successively to the desired value (35%) within 6 hours.
8. The solvent-filled phosgenation tower (1200) was heated up to 105° C. with the aid of a heat transfer agent. As soon as the phosgene solution concentration reached 25%, the MDA feed was opened. During the startup, a stoichiometric excess of phosgene to MDA of 140% was established; the production capacity was 15% of the desired value of 25.45 t/h of MDI. The MDA flow rate was increased to 25% of the target production capacity after 1 h. On attainment of this load, a stoichiometric excess of phosgene to MDA of 100% was established. The MDA concentration in solvent was then adjusted to 28%; the concentration of phosgene in the phosgene solution (30) had now reached 35%.
9. As soon as the first crude MDI, solvent and phosgene arrived in the dephosgenation column (B.I), 2100) from the overflow from the phosgenation tower (1200) of the reaction section, it was adjusted, at a pressure of 1.6 bar (absolute), to a target temperature in the distillation bottoms of 157° C. in the dephosgenator bottom and was thus in operation.
10. As soon as the first hydrogen chloride found its way via the phosgene absorption (B.I), 2500) into the hydrogen chloride absorption (B.II), 2600) after the start of the phosgenation, the hydrochloric acid concentration in the outflow from the hydrochloric acid absorber (2600) was adjusted to 31%. The pathway of the hydrochloric acid to the hydrochloric acid tank (2610) was opened and the pathway to the dilute acid tank (2620) was closed. Then the hydrogen chloride absorption was in operation. This operation took 2 hours and ran in parallel with the startup of the phosgenation.
11. As soon as the pressure at the top of the second solvent distillation column (B.I), 2300; for reasons of drawing simplicity, FIG. 3 shows just one column) had settled out at 70 mbar (absolute) and a bottom temperature of 120° C. had been attained, the bottoms from this second solvent distillation column were switched to the inflow of the distillation apparatus for removal of polymeric isocyanate fractions (B.I), 2410). The polymeric bottom product was pumped into an MDI product tank. The monomeric MDI that was obtained at the top of the column was purified in further columns (B.I), 2400).
12. Then the MDI plant was running at 25% of the target production capacity, and the load was gradually increased further. The target production capacity of 25.45 t/h of MDI was not established until on-spec product was obtained in the distillation (B.III), 2410, 2400). This took 12 hours.

Assessment of the Energy and Auxiliaries Required and Time Taken for the Running Down and Starting Up of the Plant Including the Fixing of the Leak:

The total time taken for the measure until the production plant was again providing on-spec product with the target capacity of 25.45 t/h of MDI was 64 hours. This reduced the production volume by 1629 tonnes of MDI. The nitrogen consumption during the repair measure (3 hours) and during the inertization of the plant with nitrogen (6 hours) was 450 m$^3$ (STP). The natural gas consumption for the offgas incineration (D), 6000) during the measure was 8450 m$^3$ (STP).

Example 2 (Inventive): Brief Shutdown of an MDI Production Plant, Comprising a Partial Shutdown of the Production Plant, the Establishment of Circulation Modes for Plant Components that have not been Shut Down, the Performance of a Repair Measure and Restarting of the Production Plant The production plant was operated as described under A. As shown in FIG. 3, there were two (identically constructed) phosgene breakdown units (3011, 3012). The first phosgene breakdown unit (3011) serves exclusively to accommodate process offgas. The second phosgene breakdown unit (3012) is used solely for oxygen-containing offgas streams. There is no solvent adsorption stage connected between the second phosgene breakdown unit (3012) and the offgas incineration. In regular operation, these are merely streams from sampling points that are obtained from time to time; but the unit (3012) was permanently kept ready for operation. A pipeline grid made of electrically conductive polyethylene having closable connections for movable hoses was available in all regions of the production plant in order to conduct oxygen-rich offgases to this second phosgene breakdown unit (3012). Process offgas (210-X) from the first phosgene breakdown unit (3011) and oxygen-containing offgas (410-X) from the second phosgene breakdown unit (3012) are conducted separately from one another into the offgas incineration (D, 6000) and incinerated therein.

A leak occurred in the vapor conduit for the process offgas stream (70) from a phosgenation tower (1200) into the phosgene absorption (2500), which was fixed by proceeding as follows:

1. The gas exit from the phosgenation tower (1200), for stream (70) in regular operation, was opened via the fixedly connected pipeline grid by opening a valve to the second phosgene breakdown unit (3012). Connections from the reaction section (A, 1000) to the other parts of the production plant that are used in regular operation were closed by the closing of the appropriate valves. The pressure in the phosgenation tower dropped to 930 mbar (absolute). At the leakage site (that was between the exit from the phosgenation tower (1200) and the valve—now closed—in the conduit for stream (70) in regular operation), a hose was connected, by means of which a connection to the second phosgene breakdown unit (3012) was established; here too, a pressure of 930 mbar (absolute) was established.
2. The supply of MDA was stopped, which resulted directly in a drop in the temperature in the mixing unit (1100). The supply of MCB from the tank (1040) was maintained for another 3 minutes; phosgene solution from the tank (1030) was supplied further for 30 seconds, then both streams were likewise shut down. The reaction solution that remained in the phosgenation tower was emptied via an emergency outlet into an emergency discharge vessel (not shown in FIG. 3), which took 15 minutes. This emergency discharge vessel was connected to the first phosgene breakdown unit (3011). After the phosgenation tower had been emptied, the offgas pathway to the first phosgene breakdown unit (3011), which runs via the phosgene absorption (B.I), 2500), was closed directly beyond the gas exit from the emergency discharge vessel. The emergency discharge vessel was now no longer connected to the phosgene absorption (B.I), 2500), but was connected to the second phosgene breakdown unit (3012) via a fixedly connected offgas conduit by opening a valve, in order to remove oxygen-containing offgas (400-X) thereto (see also FIG. 2, although the emergency discharge vessel was omitted for reasons of drawing simplicity).
3. After switching off the MDA supply, the phosgene preparation (0, 4000, 4010) was stopped and all inlets and outlets into it were closed. This took 3 minutes.
4. The vapor conduit affected was purged with MCB, then adhering MCB was driven out by introduction of nitrogen. The MCB used for purging was conducted into the emergency discharge vessel.
5. After the emergency shutdown of the reaction under numeral 1, the dephosgenation column (B.I), 2100), the solvent distillation (B.I), 2200), the solvent purification (B.I), 2300), the unit for polymer removal (B.III), 2410), the distillation apparatus (B.III), 2400) and the hydrogen chloride absorption (B.II), 2600) were put into circulation mode. This was accomplished as elucidated further up with reference to figures FIG. 4a and FIG. 4b. The gaseous exit streams from the dephosgenation (90-X) and the solvent distillation (130-X) flowed here through the phosgene absorption (B-I), 2500) and thence as stream (170-X) into the hydrogen chloride absorption (B.II), 2600). The phosgene absorption (B.I), 2500) remained here at its standard operating pressure (1.6 bar (absolute)); only feeding of fresh MCB from the solvent tank (1040) to the top of the phosgene absorption was closed. By contrast with the comparative example, the vacuum system of the distillation apparatuses (2200), (2300), (2410) and (2400) was kept in operation.
6. The refrigeration for cooling of MCB was likewise kept in operation.
7. The entire offgas workup (C, 3000) remained in operation. A total of 198 minutes elapsed from initiation of the emergency shutdown until the preparation of the plant for the maintenance measure was complete.

Procedure for the Repair Measure

To fix the leak in the seal in the vapor conduit in question in the phosgenation tower, a seal was changed. This was done with maintenance of the reduced pressure of 930 mbar (absolute). After installation of the new seal, the connection to the second phosgene breakdown unit (3012) was closed for isolation from the reduced pressure and to perform a leak test with nitrogen. Thereafter, the reaction section (A, 1000) was purged with nitrogen in order to remove the very last traces of oxygen. The time taken for the repair was 3 hours, and that for the purging with nitrogen 1 hour.

The change of the faulty seal took a total of 7.3 hours.

Restarting of the Production Plant

The procedure was as follows:

1. MCB was pumped out of the solvent tank (1040) into the emptied reaction section. After 6 hours, there was a sufficient liquid level (MCB ran out of the phosgenation tower across into the dephosgenation column). The dephosgenation column was then put into operation.
2. The phosgene production (0, 4000, 4010) was started up, and the phosgene concentration in the phosgene dissolution tank (1030) was concentrated successively to the desired value (35%) within 6 hours.
3. The solvent-filled phosgenation tower (1200) was heated up to 105° C. with the aid of a heat transfer agent. As soon as the phosgene solution concentration reached 25%, the MDA feed was opened. During the startup, a stoichiometric excess of phosgene to MDA of 140% was established; the production capacity was 15% of the desired value of 25.45 t/h of MDI. The MDA flow rate was increased to 25% of the target production capacity after 1 h. On attainment of this load, a stoichiometric excess of phosgene to MDA of 100% was established. The MDA concentration in the solvent was then adjusted to 28%; the concentration of phosgene in the phosgene solution (30) had now reached 35%.
4. As soon as the first crude MDI, solvent and phosgene arrived in the dephosgenation column (B.I), 2100) from the overflow from the phosgenation tower (1200) of the reaction section, it was adjusted, at a pressure of 1.6 bar (absolute), to a target temperature in the distillation bottoms of 157° C. in the dephosgenator bottom and was thus in operation.
5. As soon as the first hydrogen chloride found its way via the phosgene absorption (B.I), 2500) into the hydrogen chloride absorption (B.II), 2600) after the start of the phosgenation, the hydrochloric acid concentration in the outflow from the hydrogen chloride absorber (2600) was adjusted to 31%. The pathway of the hydrochloric acid to the hydrochloric acid tank (2610) was opened and the pathway to the dilute acid tank (2620) was closed. Then the hydrogen chloride absorption was in operation. This operation took 2 hours and ran in parallel with the startup of the phosgenation.

6. As soon as the pressure at the top of the second solvent distillation column (B.I), 2300); for reasons of drawing simplicity, FIG. 3 shows just one column) had settled out at 70 mbar (absolute) and a bottom temperature of 120° C. had been attained, the bottoms from this second solvent distillation column were switched to the inflow of the distillation apparatus for removal of polymeric isocyanate fractions (B.I), 2410). The polymeric bottom product was pumped into an MDI product tank. The monomeric MDI that was obtained at the top of the column was purified in further columns (B.I), 2400) to give the desired composition of the isomers.

7. Then the MDI plant was running at 25% of the target production capacity, and the load was gradually increased further. The target production capacity 25.45 t/h of MDI was not established until on-spec product was obtained in the distillation (B.III), 2410, 2400). This took 8 hours.

Assessment of the Energy and Auxiliaries Required and Time Taken for the Running Down and Starting Up of the Plant Including the Fixing of the Leak:

The total time taken for the measure until the production plant was again providing on-spec product with the target capacity of 25.45 t/h was 29 hours and 18 minutes. This reduced the production volume by 746 tonnes of MDI. Nitrogen consumption during the repair measure (1 hour) and during the inertization of the plant with nitrogen (1 hour) was 100 m$^3$ (STP). The natural gas consumption for the offgas incineration (D), 6000) during the measure was 3211 m$^3$ (STP).

Conclusion: In inventive example 2 with two separately installed phosgene breakdown units (3011, 3012) and in circulation mode of the unaffected plant components, 61% primary energy (steam and power) and about 80% nitrogen less were consumed than in the event of a complete shutdown of the plant as in example 1 (comparative example). In addition, greatly improved productivity of the plant is found, since 908 tonnes more of MDI were producible because of the shorter time taken for the whole operation (running down, measure and startup).

The invention claimed is:

1. A method of operating a production plant for preparation of a chemical product by reacting an H-functional reactant with phosgene in the event of a production stoppage, wherein the production plant has the following plant components:
   A) a reaction section suitable for reacting the H-functional reactant with phosgene, the reaction section comprising:
   A.I) a mixing zone for mixing the H-functional reactant and phosgene to give a reaction mixture, and
   A.II) a reaction zone connected to the mixing zone for reacting the reaction mixture obtained in A.I) to form a liquid phase comprising the chemical product and phosgene and a first phosgene-containing process offgas stream;
   B) a workup section connected to the reaction section and having, the workup section comprising:
   B.I) a separation unit for separating the liquid phase obtained in A.II) into a second phosgene-containing process offgas stream and into a liquid phase comprising the chemical product;
   C) an offgas workup section suitable for workup of phosgene-containing offgas streams obtained during the preparation of the chemical product and during the production stoppage, the offgas workup section comprising a first phosgene breakdown unit and a second phosgene breakdown unit, where the first phosgene breakdown unit and the second phosgene breakdown unit are configured to receive inflow of phosgene-containing offgas streams independently of one another; and
   D) an incineration unit suitable for incineration of the worked-up offgas obtained in the offgas workup section;

wherein phosgene is used in a stoichiometric excess relative to all active hydrogen atoms of the H-functional reactant during the preparation of the chemical product in the reaction section, wherein the first phosgene-containing process offgas stream obtained from A.II) in the reaction zone and the second phosgene-containing process offgas stream obtained from B.I.) in the separation unit, each optionally after passing through further workup steps, are sent to the first phosgene breakdown unit, the method comprising switching off the supply of the H-functional reactant to interrupt production of the chemical product during the time period from the production stoppage until a restart of production, wherein, during the interruption, at least one plant component of A) and/or B) is shut down and, in at least one of the plant components that have not been shut down, an output stream therefrom is conducted
   (i) into the plant component that has not been shut down or
   (ii) into an upstream or downstream plant component of the plant component that has not been shut down and then, optionally via further plant components that have not been shut down, recycled into the plant component that has not been shut down thereby putting the plant component that has not been shut down and, in the case of (ii), additionally the plant component upstream or downstream thereof and any further plant components that have not been shut down in a circulation mode, wherein process offgas is obtained in the at least one plant component put in circulation mode and oxygen-containing offgas is obtained in the at least one plant component that has been shut down;

process offgas from the at least one plant component that was put in circulation mode is conducted into the first phosgene breakdown unit, wherein the first phosgene breakdown unit remains in operation even during the production interruption;

oxygen-containing offgas from the at least one plant component that was shut down is supplied to the second phosgene breakdown unit, wherein the second phosgene breakdown unit is in operation at least during the production interruption, and process offgas that was freed of phosgene from the first phosgene breakdown unit and oxygen-containing offgas that was freed of phosgene from the second phosgene breakdown unit are supplied separately to and combusted in the incineration unit at spatially separate points.

2. The method of claim 1, in which the chemical product is an organic carbonate.

3. The method of claim 1, in which the chemical product is an isocyanate.

4. The method of claim 3, in which the separation unit from B.I) comprises:
- a first distillation apparatus for separating the liquid phase into a liquid stream comprising solvent and isocyanate and a third phosgene-containing process offgas stream comprising phosgene and hydrogen chloride;
- a second distillation apparatus for separating the liquid stream comprising solvent and isocyanate into a process offgas stream comprising solvent and a liquid stream comprising isocyanate;
- a third distillation apparatus for separating the process offgas stream comprising solvent into a liquid stream comprising solvent and a fourth, phosgene-containing process offgas stream.

5. The method of claim 4, in which the separation unit from B.I) also comprises an absorption apparatus in which the first phosgene-containing process offgas stream, the third phosgene-containing process offgas stream and the fourth phosgene-containing process offgas stream are cleaned by absorption in a solvent to obtain a liquid stream comprising solvent and phosgene and a gaseous process offgas stream comprising hydrogen chloride and solvent, wherein the first phosgene-containing process-offgas stream and the third phosgene-containing process offgas stream are combined and the combined phosgene-containing process offgas stream and the fourth phosgene-containing process offgas stream are each condensed and then introduced in liquid form into the absorption apparatus.

6. The method of claim 5 in which the workup section from B) comprises, in addition to the separation unit from B.I),
- B.II) a separation unit for separation of hydrogen chloride from the second phosgene-containing process offgas stream in which the second phosgene-containing process offgas stream is depleted of hydrogen chloride, wherein a fifth gaseous phosgene-containing process offgas stream comprising solvent and any gaseous secondary components is obtained, wherein the fifth phosgene-containing process offgas stream is sent to the first phosgene breakdown unit.

7. The method of claim 6, in which the separation of the hydrogen chloride in the separation unit is performed by absorption of hydrogen chloride in water or hydrochloric acid at a concentration in the range from 0.50% by mass to 15.0% by mass, based on the total mass of the hydrochloric acid, to obtain a hydrochloric acid-containing stream in addition to the fifth phosgene-containing process offgas stream comprising solvent and any gaseous secondary components.

8. The method of claim 6, in which the workup section from B) comprises, in addition to the separation unit from B.I) and the separation unit from B.II),
- B.III) a distillation unit for workup of the liquid phase comprising the isocyanate,
- wherein the distillation unit is optionally preceded upstream by a unit for removing polymeric isocyanate fractions.

9. The method of claim 8, wherein the unit for removing polymeric isocyanate fractions is present, in which circulation modes are established during the production interruption, the circulation modes comprising:
- a first circulation mode proceeding from the top of the second distillation apparatus via the third distillation apparatus back into the second distillation apparatus;
- a second circulation mode proceeding from the bottom of the second distillation apparatus via the unit for removing polymeric isocyanate fractions back into the second distillation apparatus;
- a third circulation mode proceeding from the first distillation apparatus and back thereto, and
- a fourth circulation mode proceeding from the separation unit for separating hydrogen chloride and back thereto, and
- wherein the reaction section from A) is shut down.

10. The method of claim 1, in which the production plant comprises a phosgene preparation section comprising an apparatus for preparing phosgene from carbon monoxide and chlorine, wherein the preparation of phosgene is shut down when production is interrupted, optionally with a time delay after the supply of the H-functional reactant has been switched off.

11. The method of claim 1, in which the plant components of the workup section from B) are operated at least partially at reduced pressure relative to ambient pressure, wherein the reduced pressure is generated by vacuum generation plants in which process offgas streams that are supplied to the first phosgene breakdown unit are obtained.

12. The method of claim 11, in which the first phosgene breakdown unit has at least two separately operated phosgene breakdown plant components, wherein, during the preparation of the chemical product, one of the two phosgene breakdown plant components is supplied solely with the process offgas streams from the vacuum generation plants, while the other phosgene breakdown plant component is supplied with all other process offgas streams, wherein, during a production stoppage, the vacuum generation plants are shut down and remain connected to the phosgene breakdown plant component.

13. The method of claim 1, in which, during the production of the chemical product, oxygen-containing offgas streams are obtained, wherein the second phosgene breakdown unit for oxygen-containing offgas streams is operated during the production of the chemical product and the second phosgene breakdown unit is supplied with the oxygen-containing offgas streams.

14. The method of claim 13, in which the second phosgene breakdown unit comprises at least two phosgene breakdown plant components connected in parallel, wherein one of the phosgene breakdown plant components is supplied solely with the oxygen-containing gas streams obtained during the production of the chemical product, while the other phosgene breakdown plant component is supplied with the oxygen-rich offgas streams obtained in at least one plant component shut down in the event of a production stoppage.

15. The method of claim 2, in which the organic carbonate comprises a polycarbonate.

16. The method of claim 3, in which the isocyanate comprises tolylene diisocyanate or a mixture of methylene diphenylene diisocyanate and polymethylene polyphenylene polyisocyanate.

17. The method of claim 6 wherein the second phosgene-containing process offgas stream depleted of hydrogen chloride passes through a vapor condenser before the fifth gaseous phosgene-containing process offgas stream comprising solvent and any gaseous secondary components is obtained.

\* \* \* \* \*